United States Patent
Wang et al.

(10) Patent No.: US 10,633,414 B2
(45) Date of Patent: Apr. 28, 2020

(54) TANDEM FOLDING METHODS TO IMPROVE PROTEIN FOLDING YIELD

(71) Applicant: Purdue Research Foundation, West Lafayette, IN (US)

(72) Inventors: Nien-Hwa Linda Wang, West Lafayette, IN (US); Chongli Yuan, West Lafayette, IN (US); Morgan H. Crawford, Jersey City, NJ (US)

(73) Assignee: Purdue Research Foundation, West Lafayette, IN (US)

( * ) Notice: Subject to any disclaimer, the term of this patent is extended or adjusted under 35 U.S.C. 154(b) by 244 days.

(21) Appl. No.: 15/748,012

(22) PCT Filed: Jul. 27, 2016

(86) PCT No.: PCT/US2016/044278
§ 371 (c)(1),
(2) Date: Jan. 26, 2018

(87) PCT Pub. No.: WO2017/019776
PCT Pub. Date: Feb. 2, 2017

(65) Prior Publication Data
US 2018/0354985 A1     Dec. 13, 2018

Related U.S. Application Data

(60) Provisional application No. 62/197,128, filed on Jul. 27, 2015.

(51) Int. Cl.
| | | |
|---|---|---|
| C07K 1/113 | (2006.01) | |
| C07K 1/14 | (2006.01) | |
| A61K 47/42 | (2017.01) | |
| C12R 1/19 | (2006.01) | |

(52) U.S. Cl.
CPC ............ *C07K 1/1133* (2013.01); *A61K 47/42* (2013.01); *C07K 1/14* (2013.01); *C12R 1/19* (2013.01)

(58) Field of Classification Search
None
See application file for complete search history.

(56) References Cited

U.S. PATENT DOCUMENTS 5,952,461 A     9/1999     Kim et al.

OTHER PUBLICATIONS

Boyle, DM, et al., "Evaluation of refolding conditions for a human recombinant fusion cytokine protein, promegapoietin-1a" Biotechnol. Appl. Biochem. 2008, 49, 73-83.
Moghadam, M, et al., "Refolding process of cysteine-rich proteins: Chitinase as a model." Reports of Biochemistry & Molecular Biology, 2015, 4(1), 19-24.
Petrides D., et al., Computer-Aided Process Analysis and Economic Evaluation for Biosynthetic Human Insulin Production—A Case Study. Biotechnology and Bioengineering, 1995, vol. 48, pp. 529-541.
Cowley, D.J., et al., Expression, purification and characterization of recombinant human proinsulin. FEBS Letters 402 (1997) 124-130.
Tikhonov, R.V., et al., Recombinant human insulin IX. Investigation of factors, influencing the folding of fusion protein-S-sulfonates, biotechnological precursors of human insulin. Protein Expression and Purification 26 (2002) 187-193.
Min, C-K, et al., Increased expression, folding and enzyme reaction rate of recombinant human insulin by selecting appropriate leader peptide. Journal of Biotechnology 151 (2011) 350-356.
Chen, S., et al., In Vitro Folding of Methionine-Arginine Human Lyspro-Proinsulin S-sulfonate—Disulfide Formation Pathways and Factors Controlling Yield. Biotechnol. Prog. 2010, 26: 1332-1343.
Winter, J., et al., Renaturation of human proinsulin—a study on refolding and conversion to insulin. Analytical Biochemistry 310 (2002) 148-155.
International Search Report and Opinion from PCT office, dated Oct. 21, 2016.

*Primary Examiner* — Kagnew H Gebreyesus
(74) *Attorney, Agent, or Firm* — Purdue Research Foundation; Liang Zeng Yan

(57) ABSTRACT

Methods of refolding proteins are provided, especially cysteine-containing proteins such as insulin, proinsulin, and analogues thereof. The methods make used of tandem folding via the addition, at two different time, of two different reducing agents. A first reversible reducing agent can be added to induce folding and, at a later time, a second irreversible reducing agent can be added to prevent and/or reverse the formation of aggregates via intermolecular sulfide bonds. The methods can be used to reform a variety of cysteine-containing proteins with high yield of the native form, e.g. about 60 mol %, 70 mol %, or more.

15 Claims, 22 Drawing Sheets

TANDEM FOLDING METHODS TO IMPROVE PROTEIN FOLDING YIELD

CROSS-REFERENCE TO RELATED APPLICATIONS

This application is a U.S. National Stage Application of PCT/US16/44278, filed Jul. 27, 2016, which claims priority to, and the benefit of, U.S. provisional application entitled "Tandem Folding Method Useful for Improving Proinsulin-S-sulfonate Folding Yield" having Ser. No. 62/197,128, filed Jul. 27, 2015, the contents of which are incorporated by reference in their entirety.

TECHNICAL FIELD

The present disclosure generally relates to methods of in-vitro protein refolding.

BACKGROUND

Proteins are used as pharmaceuticals for the treatment of diseases in humans and other animals. About 50% of the top selling biopharmaceutical products in 2013 were therapeutic proteins, such as insulin and interferon (IFN-α-2a).

Many pharmaceutical proteins contain cysteine residues. In proteins with more than one cysteine residue, the thiol groups of the cysteine residues are usually covalently linked with other cysteine residues by specifically paired disulfide bonds. The therapeutically active form of a protein is usually a single disulfide species. While the native form of most proteins is a single disulfide species, some may cycle between a few disulfide states as part of their function, e.g., thioredoxin. In proteins with more than two cysteines, non-native disulfide species may be formed, which are typically misfolded. As the number of cysteines increases, the number of nonnative species can increase factorially.

Proteins may be made by recombinant DNA technology in host cells in which correct disulfide bond formation does not take place. For example, therapeutic proteins are typically produced using recombinant technology and a host expression system. E. coli based expression systems are widely used because of their simplicity, low cost, and relatively high protein yield. Overexpressed proteins accumulate in cytoplasm as inclusion bodies, which are biologically inactive.

A well-designed dissolution and refolding process is required to restore their native structures and biological activity. Generally, this refolding process is considerably slower for cysteine-containing proteins due to the formation of non-native disulfide bonds. The therapeutic proteins containing cysteine residues generally require the formation of proper disulfide bonds to maintain their native structures and stability. Large yield loss during the refolding step is a common problem and contributes significantly to the high production costs of therapeutic proteins. Refolding yield is usually low because of aggregation of the folding intermediates, the formation of non-native disulfide bonds, or stable, non-native tertiary structures.

This problem of yield loss during refolding is especially important for proteins with two or more disulfide bonds, such as proinsulin, interleukins, and growth factors. Unproductive aggregation reactions compete with slow productive disulfide bond formation and reshuffling reactions, resulting in significant yield loss. Although protein refolding processes have been revamped over the past decades with the introduction of on-line monitoring, folding additives, and on-column folding, the refolding procedures still requires optimization on a case-to-case basis. The molecular events and their affiliated kinetics contributing to the yield loss during refolding processes remain elusive for many systems. No refolding methods have emerged as the universal method. There remains a need to develop a rationally designed refolding procedure for increasing the yield of therapeutic proteins.

Insulin is the only therapeutic protein that is produced on the tons-per-year scale. In 2011, global insulin sales reached $16.7 billion, most of which was generated by three companies: Novo Nordisk (41%), Sanofi-Aventis (32%), and Eli Lilly (20%).6,7 While Novo Nordisk uses a yeast expression system to produce insulin, Sanofi-Aventis and Eli Lilly produce insulin using recombinant *E. coli*. Insulin is expressed as a precursor of proinsulin and stored in the *E. coli* cells as inclusion bodies. To produce insulin, the inclusion bodies must be isolated, denatured, sulfitolyzed, and refolded to form proinsulin-S-sulfonate (hPSS). During the in vitro folding of hPSS, a significant fraction of the folding intermediates aggregate through intermolecular disulfide bond formation, resulting in a yield loss of 40% or more. Of all the process steps for manufacturing insulin, the folding step has the lowest yield. Increasing in-vitro folding yield of proinsulin can significantly increase plant productivity, reduce raw materials and wastes, and reduce the cost of insulin produced from recombinant *E. coli*.

There remains a need for improved refolding methods for therapeutic proteins, such as hPSS, that overcome the aforementioned deficiencies.

SUMMARY

A variety of methods are provided for refolding of proteins, in particular for refolding of cysteine-containing proteins useful in numerous therapeutic contexts. The proteins can include, for example, recombinant proteins, even recombinant proteins isolated from inclusion bodies of host systems such as an *Escherichia coli* expression system.

In various aspects, methods of refolding a solubilized cysteine-containing protein to its native form are provided. The methods can include adding a reversible reducing agent to a solution containing the solubilized cysteine-containing protein to initiate folding of the cysteine-containing protein, and adding an irreversible reducing agent to the solution at a time after the initiation of folding to breakdown aggregates of the cysteine-containing protein. The reversible reducing agent also converts non-native disulfide bonds into native disulfide bonds via a disulfide reshuffling process.

A variety of reversible reducing agents can be used in the methods provided herein. In various aspects, the reversible reducing agent is cysteine, cystine, cysteamine, cystamine, beta-mercaptoethanol, glutathione-reduced, glutathione-oxidized, a derivative thereof, or a combination thereof. The reversible reducing agent can be added at a ratio of [reversible reducing agent]:[thiols in the cysteine-containing protein] of about 3:1 to 4:1.

The timing for the addition of the irreversible reducing agent can have a strong influence on the yield of the native form. In some aspects, at least some of the cysteine-containing protein forms a dimer, and the time after the initiation of folding is when the concentration of the dimer in the solution is about 5 mol % to 12 mol % based upon the concentration of the cysteine-containing protein. In some aspects, at least some of the cysteine-containing protein forms a dimer, and the time after the initiation of folding is when the concentration of the dimer in the solution is about 1.5 to 3.0 times the concentration of the dimer in the solution prior to the addition of the reversible reducing agent. In various aspects, the time after the initiation of folding is about 5 minutes to 15 minutes, or about 10 minutes to 15 minutes. In various aspects, the irreversible reducing agent is added at a ratio of [irreversible reducing agent]:[thiols in the cysteine-containing protein] of about 0.5:1 to about 0.8:1.

A variety of irreversible reducing agents can be used in the methods provided herein. In various aspects, the irreversible reducing agent is dithiothreitol (DTT), tris(2-carboxyethyl)phosphine (TCEP), thioglycolic acid, a derivative thereof, or a combination thereof. The irreversible reducing agent can have a redox potential of about −0.3 V to −0.35V at a pH above 7.0. In some aspects, the irreversible reducing agent has a redox equilibrium constant of about $10^4$ or more.

The methods provided herein can be applied to refold a variety of cysteine-containing proteins. In various embodiments, the cysteine-containing protein is an enzyme, an antibody, an antigen, a hormone, or a cytokine. The cysteine-containing protein can be a recombinant protein, for example an inclusion body isolated from an *Escherichia coli* expression system. In some embodiments, the protein is insulin, an insulin analogue, a proinsulin, or a proinsulin analogue. The cysteine-containing protein can be present at large concentrations, e.g. about 0.1 g/L to 1.0 g/L or about 0.3 g/L to 10 g/L.

The methods can include dissolution of the cysteine-containing protein to form the solubilized cysteine-containing protein. A variety of methods can be used to dissolve the cysteine-containing protein, including for example addition of salts, sugars, amino acids, alcohols, etc. In various aspects, the methods include dissolution at an alkaline pH, e.g. at a pH o about 11.5-12.5. In some aspects, the methods further include dissolution at a temperature of about 4° C. to about 20° C. In a variety of aspects, the concentration of the unfolded monomer of the cysteine-containing protein is greater after the dissolution than the concentration of the unfolded monomer in the otherwise same solution except at a pH less than about 10.8. The hydrodynamic radius of the cysteine-containing protein, as determined by fluorescence correlation spectroscopy, can be within about 25% of the monomeric cysteine-containing protein's equivalent spherical radius.

In various aspects, the reversible reducing agent is cysteine-HCl, e.g. wherein the cysteine-HCl is dissolved to about 200 mM to about 900 mM at about 4° C. to 8° C. and acidic pH. The pH of the solution after the addition of the reversible reducing agent can be about 10.75 to about 10.85.

The methods provided herein can be used to refold a variety of proteins with high yields. In various aspects, the yield of the native form of the cysteine-containing protein is higher than yield of the native form for the same cysteine-containing protein refolded under the otherwise same conditions except without the addition of the irreversible reducing agent. In some aspects, the yield of the native form of the cysteine-containing protein is higher than yield of the native form for the same cysteine-containing protein refolded under the otherwise same conditions except where the irreversible reducing agent is added at the same time as the reversible reducing agent. In certain aspects, the yield of the native form of the cysteine-containing protein 70 mol % to 80 mol % based upon the concentration of the cysteine-containing protein.

Other systems, methods, features, and advantages of refolding of cysteine-containing proteins will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1A:
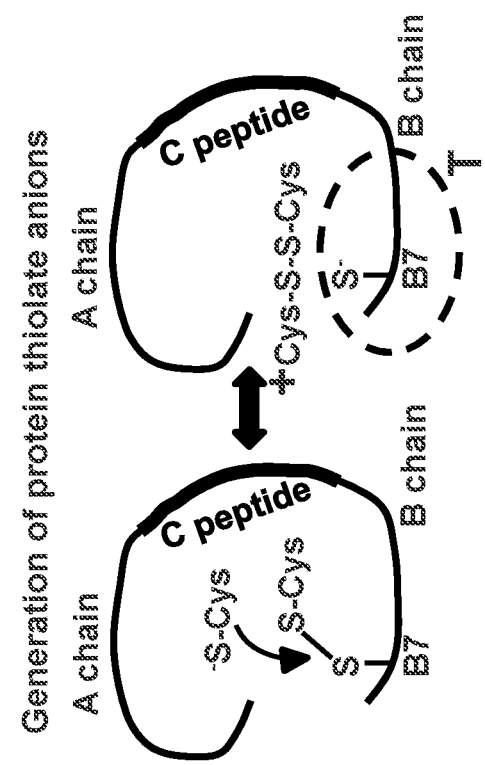
FIGS. 1A-1D depict the steps in an exemplary disulfide bond formation and disulfide bond reshuffling reactions using a cysteine/cystine redox pair.

In various aspects, methods of refolding proteins are provided, in particular of refolding a solubilized cysteine-containing protein with high yield to its native form. The methods can further include dissolution of the cysteine-containing protein prior to the initiation of folding to achieve even higher yield. In certain aspects, the yield of the native form of the cysteine-containing protein 70 mol % to 80 mol % based upon the concentration of the cysteine-containing protein.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein.

These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of biochemistry, nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "protein," as generally used herein, refers to a polymer of amino acids linked to each other by peptide bonds to form a polypeptide for which the chain length is sufficient to produce at least a detectable tertiary structure. Proteins having a molecular weight (expressed in kDa wherein "Da" stands for "Daltons" and 1 kDa=1,000 Da) greater than about 100 kDa may be designated "high-molecular-weight proteins," whereas proteins having a molecular weight less than about 100 kDa may be designated "low-molecular-weight proteins." The term "low-molecular-weight protein" excludes small peptides lacking the requisite of at least tertiary structure necessary to be considered a protein. Protein molecular weight may be determined using standard methods known to one skilled in the art, including, but not limited to, mass spectrometry (e.g., ESI, MALDI) or calculation from known amino acid sequences and glycosylation. Proteins can be naturally occurring or non-naturally occurring, synthetic, or semi-synthetic. The protein can be a recombinant protein. The term "recombinant protein," as generally used herein, refers to proteins produced from the expression of recombinant DNA within a living cell (host system). Although a variety of host systems can be employed, in various aspects the host system is a non-mammalian expression system such as *Escherichia coli*, a commonly employed host system for recombinant protein synthesis.

As used herein, the term "non-mammalian expression system" means a system for expressing proteins in cells derived from an organism other than a mammal, including but not limited to, prokaryotes, including bacteria such as *E. coli*, and yeast. Often a non-mammalian expression system is employed to express a recombinant protein of interest, while in other instances a protein of interest is an endogenous protein that is expressed by a non-mammalian cell. For purposes of the present disclosure, regardless of whether a protein of interest is endogenous or recombinant, if the protein is expressed in a non-mammalian cell then that cell is a "non-mammalian expression system." Similarly, a "non-mammalian cell" is a cell derived from an organism other than a mammal, examples of which include bacteria or yeast.

"Essentially pure protein(s)" and "substantially pure protein(s)" are used interchangeably herein and refer to a composition containing at least about 90% by weight pure protein, preferably at least about 95% pure protein by weight. "Essentially homogeneous" and "substantially homogeneous" are used interchangeably herein and refer to a composition wherein at least about 90% by weight of the protein present is a combination of the monomer and reversible di- and oligo-meric associates (not irreversible aggregates), preferably at least about 95%.

It should be noted that the terms "configuration" and "conformation," as interchangeably used herein, can describe the specific secondary, tertiary, or quaternary structure of a protein as distinguished from another secondary, tertiary, or quaternary structure of a protein having the same primary structure (same amino acid sequence).

The term "chemical stability," as generally used herein, refers to the ability of the protein components in a formulation to resist degradation via chemical pathways, such as oxidation, deamidation, or hydrolysis. A protein formulation is typically considered chemically stable if less than about 5% of the components are degraded after 24 months at 4° C.

The term "physical stability," as generally used herein, refers to the ability of a protein formulation to resist physical deterioration, such as aggregation. A formulation that is physically stable forms only an acceptable percentage of irreversible aggregates (e.g., dimers, trimers, or other aggregates) of the bioactive protein agent. The presence of aggregates may be assessed in a number of ways, including by measuring the average particle size of the proteins in the formulation by means of dynamic light scattering. A formulation is considered physically stable if less than about 5% irreversible aggregates are formed after 24 months at 4° C. Acceptable levels of aggregated contaminants ideally would be less than about 2%. Levels as low as about 0.2% are achievable, although approximately 1% is more typical.

The term "stable formulation," as generally used herein, means that a formulation is both chemically stable and physically stable. A stable formulation may be one in which more than about 95% of the bioactive protein molecules retain bioactivity in a formulation after 24 months of storage at 4° C., or equivalent solution conditions at an elevated temperature, such as one month storage at 40° C. Various analytical techniques for measuring protein stability are available in the art and are reviewed, for example, in Peptide and Protein Drug Delivery, 247-301, Vincent Lee, Ed., Marcel Dekker, Inc., New York, N.Y. (1991) and Jones, A., *Adv. Drug Delivery Revs.* 10:29-90, 1993. Stability can be measured at a selected temperature for a certain time period. For rapid screening, for example, the formulation may be kept at 40° C., for 2 weeks to one month, at which time residual biological activity is measured and compared to the initial condition to assess stability. When the formulation is to be stored at 2° C.-8° C., generally the formulation should be stable at 30° C. or 40° C. for at least one month and/or stable at 2° C.-8° C. for at least 2 years. When the formulation is to be stored at room temperature, about 25° C., generally the formulation should be stable for at least 2 years at about 25° C. and/or stable at 40° C. for at least about 6 months. The extent of aggregation following lyophilization and storage can be used as an indicator of protein stability. In some embodiments, the stability is assessed by measuring the particle size of the proteins in the formulation. In some embodiments, stability may be assessed by measuring the activity of a formulation using standard biological activity or binding assays well within the abilities of one ordinarily skilled in the art.

As used herein, the term "refolding" means a process of reintroducing secondary and tertiary structure to a protein that has had some or all of its native secondary or tertiary structure removed, either in vitro or in vivo, e.g., as a result of expression conditions or intentional denaturation and/or reduction. Thus, a refolded protein is a protein that has had some or all of its secondary or tertiary structure of the native form reintroduced. The terms "solubilization" and "dissolution," as interchangeably used herein, mean a process in which salts, ions, denaturants, detergents, reductants and/or other organic molecules are added to a solution containing a protein of interest, thereby removing some or all of a protein's secondary and/or tertiary structure and dissolving the protein into the solvent. This process can include the use of elevated temperatures, typically 4° C.-50° C., and/or alkaline pH, such as pH 10-12. Solubilization can also be accomplished by the addition of acids, such as 70% formic acid (see, e.g., Cowley & Mackin (1997) FEBS Lett 402: 124-130).

The term "native form," as generally used herein, refers to a protein that has the structural features (secondary or tertiary structure) of the protein that (a) is biologically active in an appropriate in vivo or in vitro assay designed to assess the protein's biological activity and/or (b) that has the same activity scale as found in the naturally occurring protein.

As used herein, the term "non-native form" means any form or state in which the protein (a) lacks at least one formed structural feature found in a form of the protein that is biologically active in an appropriate in vivo or in vitro assay designed to assess the protein's biological activity and/or (b) forms aggregates that require treatment, such as chemical treatment, to become soluble. The term specifically includes proteins existing in inclusion bodies, such as those sometimes found when a recombinant protein is expressed in a non-mammalian expression system. Examples of structural features characterizing a non-native form of a protein can include, but are not limited to, a lack of a particular disulfide bond, difference of quaternary structure, disrupted secondary or tertiary structure or a state that makes the protein biologically inactive in an appropriate assay. A protein in a non-native form can but need not form aggregates.

A "solubilized protein," as used herein, refers to a protein in which some or all of the protein aggregates have been removed to yield a solution of the protein having a large concentration of extended/denatured monomers, e.g. about 20 mol %, 30 mol %, 40 mol %, 50 mol %, or more of the proteins are in the extended/denatured monomer form based upon the concentration of the protein.

As used herein, the term "denaturant" means any compound having the ability to remove some or all of a protein's secondary and tertiary structure when placed in contact with the protein. The term denaturant refers to particular chemical compounds that affect denaturation, as well as solutions comprising a particular compound that affect denaturation. Examples of denaturants that can be employed in the disclosed method include, but are not limited to urea, guanidinium salts, dimethyl urea, methylurea, ethylurea and combinations thereof.

As used herein, the term "aggregation suppressor" means any compound having the ability to disrupt and decrease or eliminate interactions between two or more proteins. Examples of aggregation suppressors can include, but are not limited to, amino acids such as arginine, proline, and glycine; polyols and sugars such as glycerol, sorbitol, sucrose, and trehalose; surfactants such as, polysorbate-20, CHAPS, Triton X-IOO, and dodecyl maltoside; and combinations thereof.

As used herein, the term "protein stabilizer" means any compound having the ability to change a protein's reaction equilibrium state, such that the native state of the protein is improved or favored. Examples of protein stabilizers can include, but are not limited to, sugars and polyhedric alcohols such as glycerol or sorbitol; polymers such as polyethylene glycol (PEG) and α-cyclodextrin; amino acids salts such as arginine, proline, and glycine; osmolytes and certain Hoffmeister salts such as Tris, sodium sulfate and potassium sulfate; and combinations thereof.

The term protein "particle size," as generally used herein, means the average diameter of the predominant population of bioactive molecule particulates, or particle size distributions thereof, in a formulation as determined by using well known particle sizing instruments, for example, dynamic light scattering, SEC (size exclusion chromatography), or other methods known to one ordinarily skilled in the art.

The term "isolating," as generally used herein, means physical separation of at least one component in a mixture away from other components in a mixture. Isolating components or particular conformations of a protein can be achieved using any purification method that tends to separate such components. Accordingly, one can perform multiple chromatography steps, including but not limited to RP-HPLC, HIC, hydroxyapatite chromatography, ion exchange chromatography, affinity, and SEC. Other purification methods are filtration (e.g., tangential flow filtration), electrophoretic techniques (e.g., electrophoresis, electroelution, isoelectric focusing), and phase separation (e.g., PEG-dextran phase separation), to name just a few. In addition, the fraction of the preparation of recombinant protein that contains the protein in the undesired conformation can be treated again in the methods of the invention, to further optimize the yields of protein with the desired conformation.

A "lyoprotectant" is a substance which, when combined with a protein, significantly reduces chemical and/or physical instability of the protein upon lyophilization and/or subsequent storage. Exemplary lyoprotectants include sugars and their corresponding sugar alcohols, such as sucrose, lactose, trehalose, dextran, erythritol, arabitol, xylitol, sorbitol, and mannitol; amino acids, such as arginine or histidine; lyotropic salts, such as magnesium sulfate; polyols, such as propylene glycol, glycerol, poly(ethylene glycol), or polypropylene glycol); and combinations thereof. Additional exemplary lyoprotectants include gelatin, dextrins, modified starch, and carboxymethyl cellulose. Preferred sugar alcohols are those compounds obtained by reduction of mono- and di-saccharides, such as lactose, trehalose, maltose, lactulose, and maltulose. Additional examples of sugar alcohols are glucitol, maltitol, lactitol and isomaltulose. The lyoprotectant is generally added to the pre-lyophilized formulation in a "lyoprotecting amount." This means that, following lyophilization of the protein in the presence of the lyoprotecting amount of the lyoprotectant, the protein essentially retains its physical and chemical stability and integrity.

A "diluent" or "carrier," as generally used herein, is a pharmaceutically acceptable (i.e., safe and non-toxic for administration to a human or another mammal) and useful ingredient for the preparation of a liquid formulation, such as an aqueous formulation reconstituted after lyophilization. Exemplary diluents include sterile water, bacteriostatic water for injection (BWFI), a pH buffered solution (e.g., phosphate-buffered saline), sterile saline solution, Ringer's solution or dextrose solution, and combinations thereof.

A "preservative" is a compound which can be added to the formulations herein to reduce contamination by and/or action of bacteria, fungi, or another infectious agent. The addition of a preservative may, for example, facilitate the production of a multi-use (multiple-dose) formulation. Examples of potential preservatives include octadecyldimethylbenzylammonium chloride, hexamethonium chloride, benzalkonium chloride (a mixture of alkylbenzyldimethylammonium chlorides in which the alkyl groups are long-chained), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

A "bulking agent," as generally used herein, is a compound which adds mass to a lyophilized mixture and contributes to the physical structure of the lyophilized cake (e.g. facilitates the production of an essentially uniform lyophilized cake which maintains an open pore structure). Exemplary bulking agents include mannitol, glycine, lactose, modified starch, poly(ethylene glycol), and sorbitol.

A "therapeutically effective amount" is the least concentration required to effect a measurable improvement or prevention of any symptom or a particular condition or disorder, to effect a measurable enhancement of life expectancy, or to generally improve patient quality of life. The therapeutically effective amount is dependent upon the specific biologically active molecule and the specific condition or disorder to be treated. Therapeutically effective amounts of many proteins, such as the mAbs described herein, are well known in the art. The therapeutically effective amounts of proteins not yet established or for treating specific disorders with known proteins, such as mAbs, to be clinically applied to treat additional disorders may be determined by standard techniques which are well within the craft of a skilled artisan, such as a physician.

As used herein, the term "pharmaceutically acceptable salts" refers to salts prepared from pharmaceutically acceptable non-toxic acids and bases, including inorganic acids and bases, and organic acids and bases. Suitable non-toxic acids include inorganic and organic acids such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Suitable positively charged counterions include sodium, potassium, lithium, calcium and magnesium.

The term "formulating," as used herein, is meant that the proteins can be buffer exchanged, sterilized, bulk-packaged and/or packaged for a final user. For purposes of the disclosure, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can include an effective amount of the protein, in combination with other components such as a physiologically acceptable diluent, carrier, and/or excipient.

As used herein, the term "reversible reducing agent" means any thiol-reactive chemical or solution containing such a chemical that facilitates a reversible thiol exchange with another thiol or the cysteine residues of a protein. Examples of such compounds include, but are not limited to, glutathione-reduced, glutathione-oxidized, cysteine, cystine, cysteamine, cystamine, beta-mercaptoethanol and combinations thereof.

As used herein, the term "irreversible reducing agent" means any thiol-reactive chemical or solution containing such a chemical that facilitates an irreversible thiol exchange in the sense that the irreversible reducing agent does not regenerate. Examples of such compounds include, but are not limited to, dithiothreitol (DTT), tris(2-carboxyethyl) phosphine (TCEP), thioglycolic acid, derivatives thereof, and combinations thereof.

Refolding of hPSS

Manufacturing of insulin by the intracellular proinsulin. Method typically involves refolding of a chemically denatured proinsulin in which sulfite groups are added to the cysteine residues to prevent refolding to a non-native isomer. Proinsulin is refolded by adding a reducing agent to generate free thiol groups FIG. 1B. The native structure of proinsulin contains 6 cysteine residues with 3 disulfide bonds. The refolding pathways of proinsulin-S-sulfonate (hPSS) are described as an exemplary cysteine-containing protein.

Detailed Pathways for hPSS Folding In Vitro

Figure 1C:
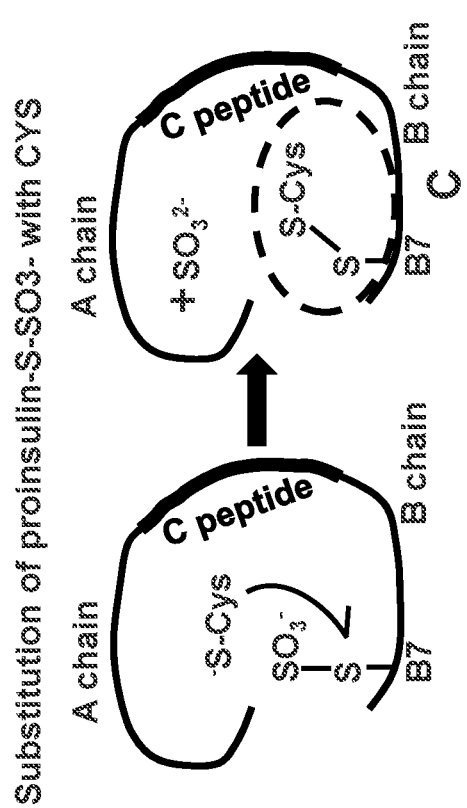
Figure 1B:
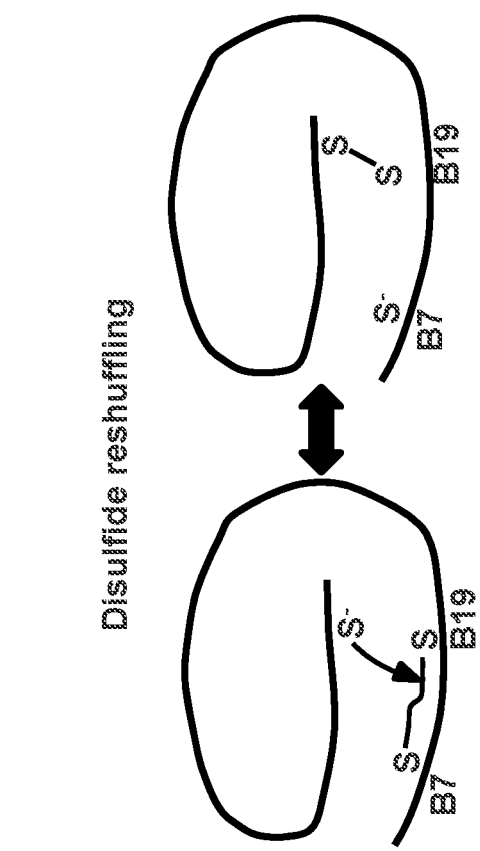
Figure 1D:
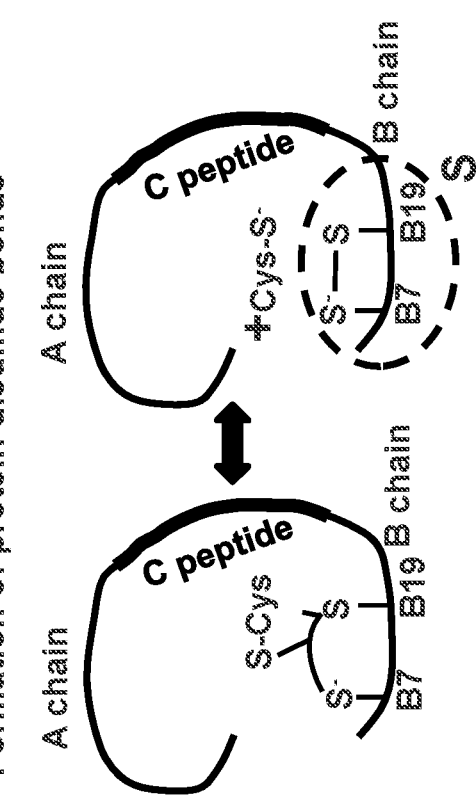

To identify the conditions that affect folding yield, it is important to understand first the folding pathways. Frozen hPSS solutions were provided by Eli Lilly Co. The frozen solution was thawed and dissolved in water at 5° C. Cysteine, a reducing agent, was added to a well-mixed solution of hPSS at 5° C. and a high pH (10.5 to 12). The protein —$SO_3$ groups were immediately displaced by cysteine thiolate anions (Cys, FIG. 1A). Subsequent disulfide exchange reactions generates protein thiolate anions (FIG. 1B), which in turn form protein disulfide bonds (FIG. 1C). Non-native protein disulfide bonds can be corrected via a slow disulfide reshuffling process (FIG. 1D). The thawing/dissolution procedure, the folding temperature, the pH, and the redox agent concentration have been found to affect folding yield. The folding intermediates were detected and characterized using matrix-assisted laser desorption ionization mass spectrometry (MALDI-MS), reversed-phase chromatography (RPC), size-exclusion chromatography (SEC), and gel electrophoresis. The folding kinetics and yield depended on the protein and cysteine concentrations. RPC coupled with MALDI-MS analyses indicated a sequential formation of intermediates with one (1S), two (2S), and three (3S) disulfide bonds. The MALDI-MS analysis of Glu-C digested, purified intermediates indicated that the native intra-A-chain disulfide bond among A6 and A11 formed first, within a few minutes after the addition of cysteine. Various nonnative intra-A (A20-A7), intra-B (B7-B19), and inter-A-B disulfide bonds were observed in the 2S intermediates. The 3S intermediates contained mainly the nonnative intra-A and intra-B bonds. At a higher cysteine-to-proinsulin-SH ratio, some of the disulfide bonds in the 2S and 3S intermediates and the folded hPI were reduced to proteins with thiolate anions, which caused unfolding and significant yield loss. At an optimal cysteine-to-proinsulin-SH ratio of 3.5, all intermediates with the nonnative disulfide bonds were converted in 24 hours to properly folded proinsulin via a slow disulfide-bond reshuffling step. Aggregation via the formation of intermolecular disulfide bonds of the early intermediates, 0S, 1S, and 2S, was the major cause of yield loss, about 40%.

Since protein folding is a first order reaction respect to protein concentration and protein aggregation is a second- or higher-order reaction, by decreasing the protein concentration to 0.1 g/L or lower can suppress the aggregation reaction. However, such a low protein concentration results in a large amount of buffer, a large reactor, and disposal of a huge volume of waste. For this reason, in many aspects the concentration of proinsulin in the folding step is about 1 g/L for insulin production.

Figure 3:
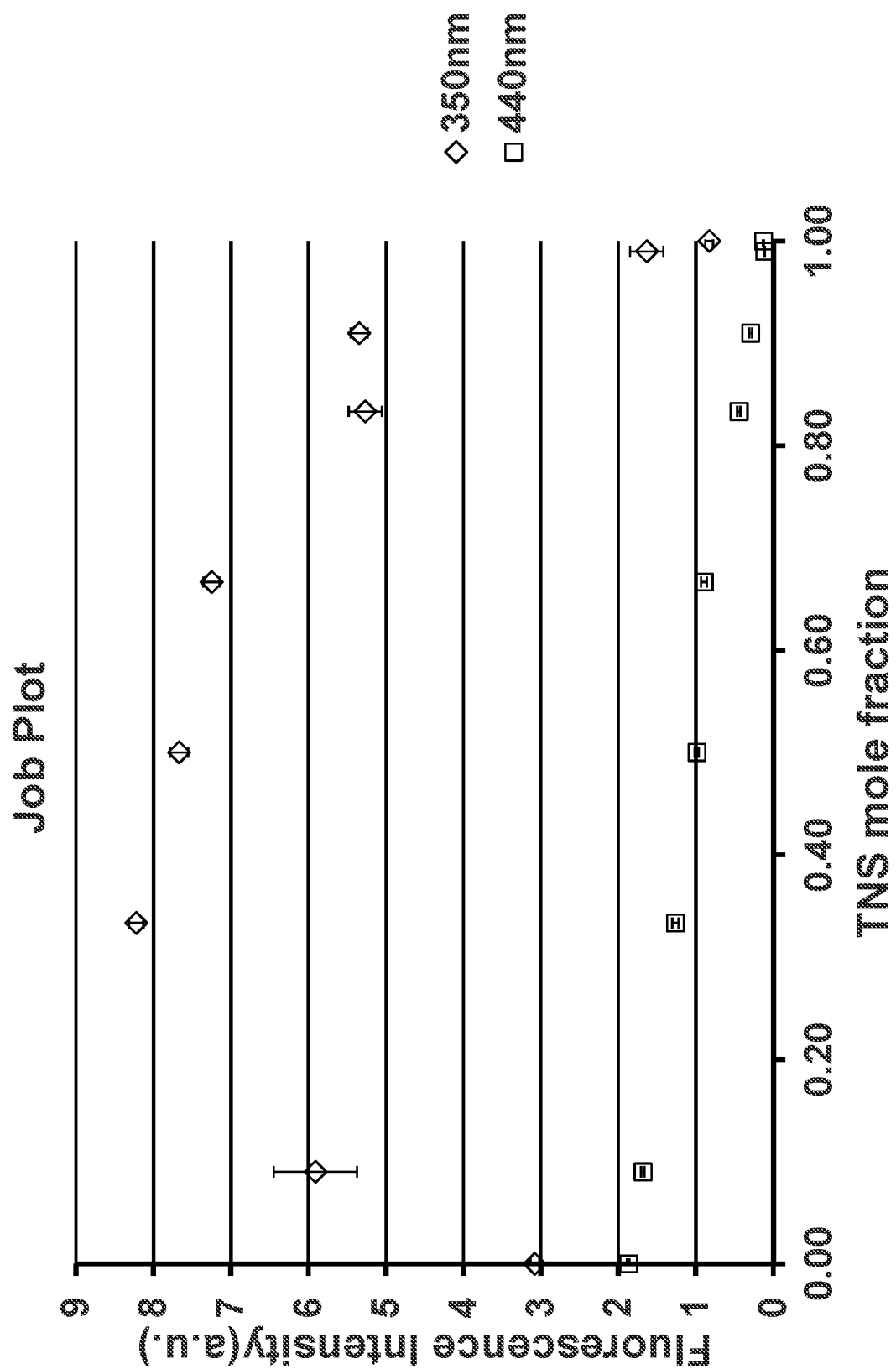
FIG. 3 is a graph of the mean fluorescence intensity of hPSS with TNS as a function of TNS mole fraction. The total concentration ([hPSS]+[TNS]) is 100 μM. Diamonds represent data at an excitation wavelength of 350 nm with the fluorescence emission recorded at 425 nm. Squares represent data at an excitation wavelength of 440 nm with the fluorescence emission recorded at 515 nm.

Our studies showed that the physical (non-covalent) factors found to affect folding yield are (1) thawing conditions of frozen hPSS, (2) hPSS dissolution conditions (pH, temperature, mixing speed, and mixing time), (3) salt concentrations in the hPSS solution, and (4) state of cysteine addition (added as a solid or as a solution). It is important to monitor the size and the structures of the folding intermediates under various dilution and folding conditions and in the presence of various folding additives. Traditional analyses of the size of folding intermediates involve LC-MS or CD measurements. These methods require large time investments and are not practical for high-throughput screening. Fluorescence Correlation Spectroscopy (FCS) methods can be used to follow the average size of hPSS during dilution, cysteine addition, and folding. FCS records the fluctuations of fluorescence signals within a small focal volume (~fl). The fluctuation data can be analyzed to reveal information about the translational diffusivity of the labeled molecules, which can be related to hydrodynamic radii (FIG. 3). This technique is highly sensitive ($10^{-12}$ M), requires only a small sample (10-50 microliters), and each measurement only takes a few minutes. This approach has been used to monitor the formation of protein oligomers and aggregates, as well as the aggregate size during various biological processes. Compared with conventional LC-MS, CD, and scattering based approaches, FCS can provide a richer body of information regarding protein aggregates and kinetics.

Tandem Folding Agents and Timely Addition of the Two Folding Agents

Figure 16A:
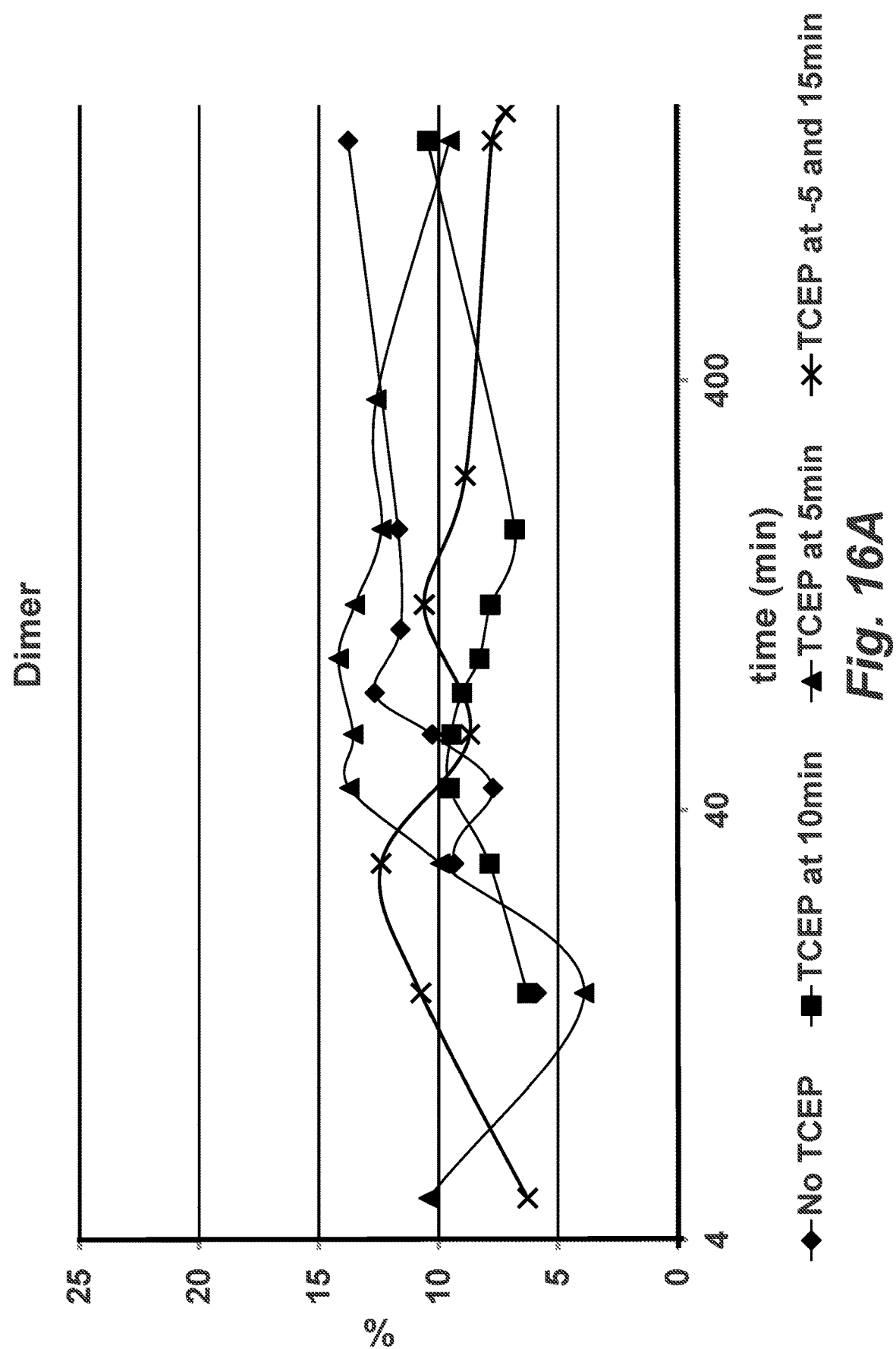
FIGS. 16A-16C are graphs of the aggregate concentrations (mol %) during folding of hPSS using one folding agent (cysteine) or two folding agents (cysteine and TCEP), depicting the dimer (FIG. 16A), trimer (FIG. 16B) and larger aggregates (FIG. 16C) as a function of time.
Figure 16B:
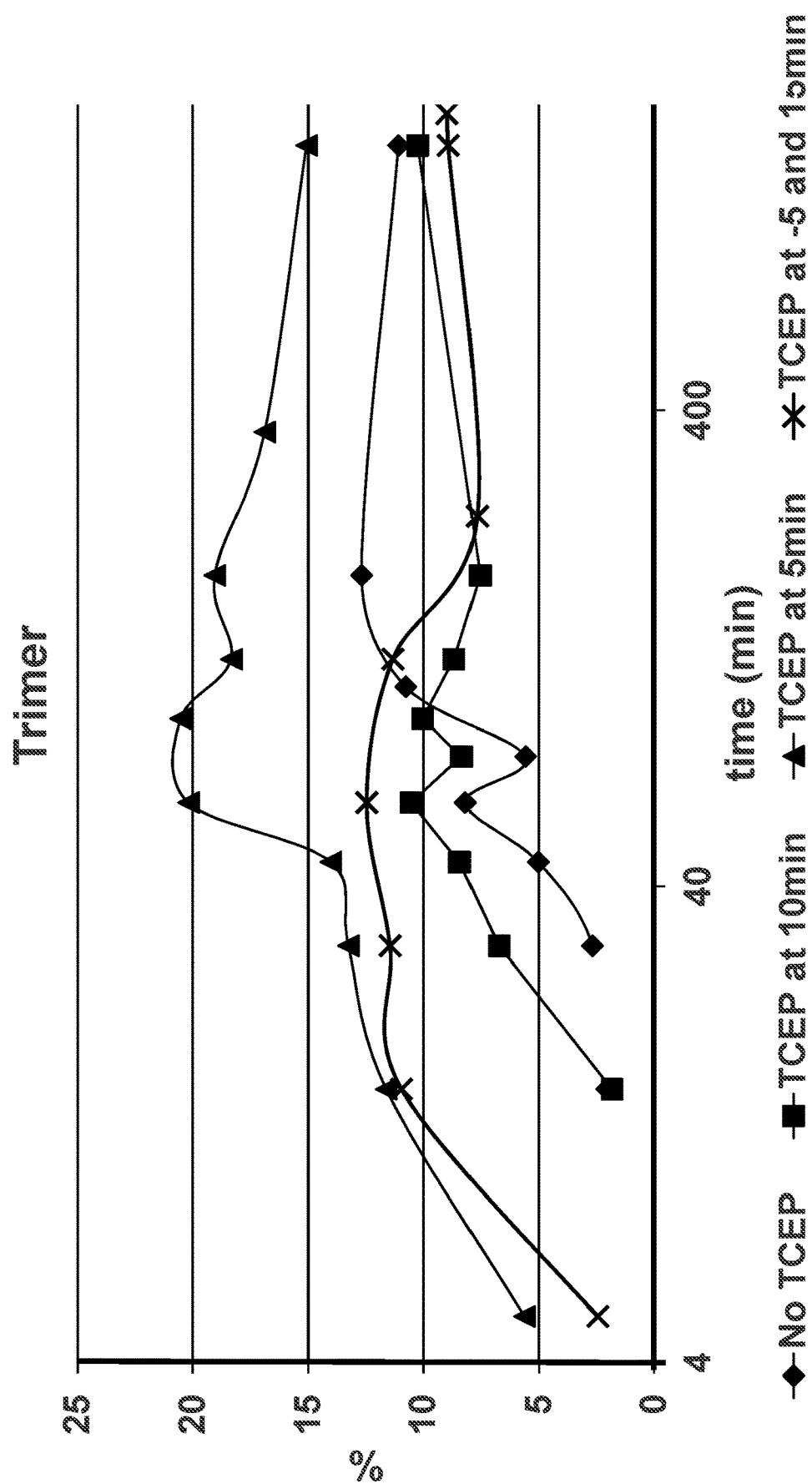
Figure 16C:
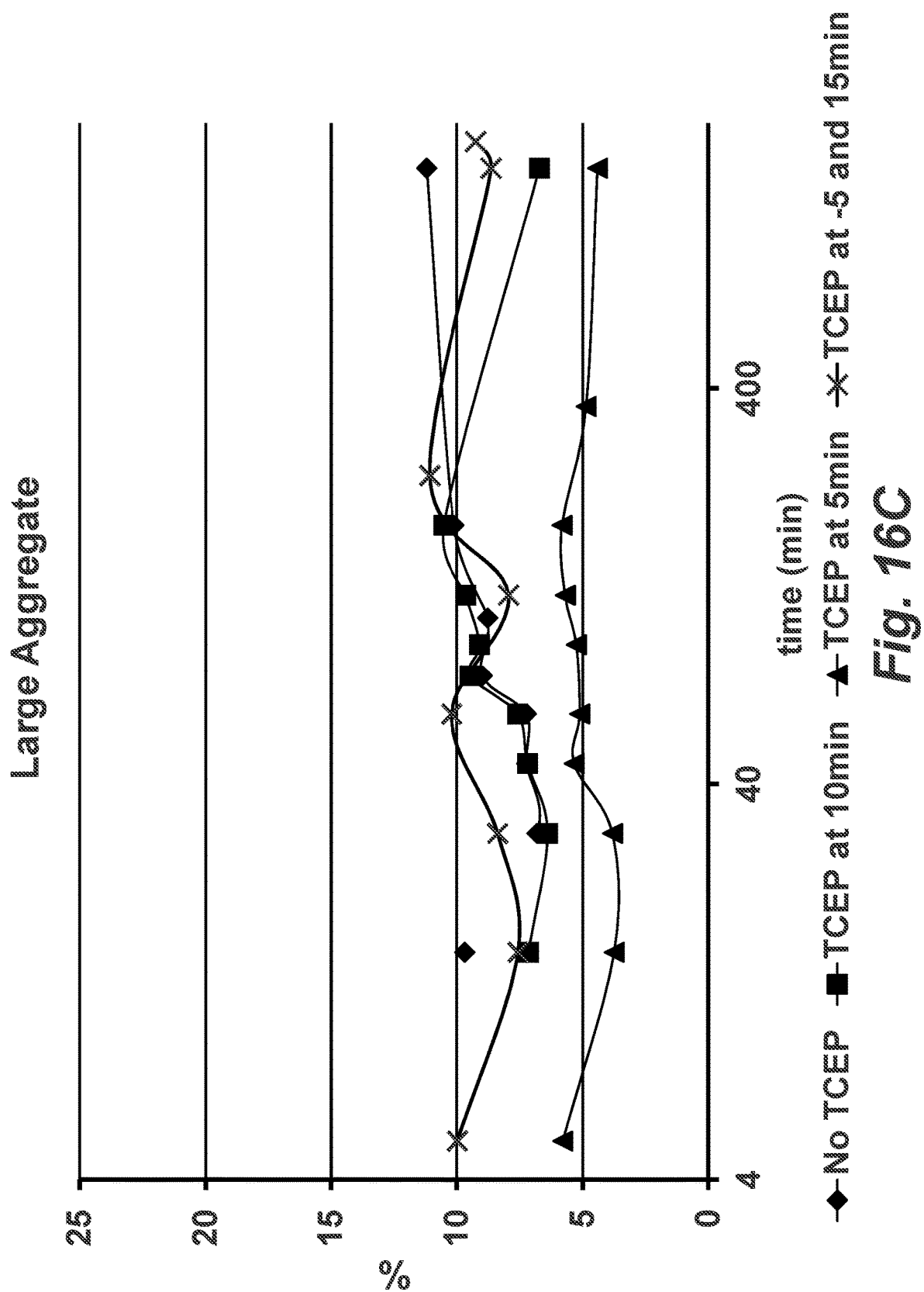

In addition to controlling the physical conditions of folding, the results of FCS, SEC, and RPC in our preliminary studies indicate that most of the aggregation reactions occur in the first hour of folding, while hPSS exists as extended monomers. The aggregation reactions due to intermolecular disulfide bond formation compete strongly with the productive reactions involving the formation of intramolecular disulfide bonds. The experimental results and the subsequent theoretical analysis using a detailed kinetics model revealed that a single pair of redox agent (cysteine/cysteine) cannot promote the disulfide exchange reactions in the productive folding pathway and at the same time inhibit the nonproductive aggregation reactions. To overcome this fundamental limitation of a single redox pair, provided herein are new tandem folding methods that use (first) a reversible reducing agent followed, at some time later, by a (second) irreversible reducing agent. A small amount of a second strong reducing agent, which favors the breakage of disulfide bonds, was added in addition to the cysteine/cysteine pair, after the first native bond A6-A11 was formed. The results showed that the timely addition of dithiothreitol (DTT) or tris(2-carboxyethyl)phosphine (TCEP) reduces the amount of dimers, trimers, and larger aggregates in the folding intermediates (FIGS. 16A-16C). A small portion of the yield was recovered by converting dimers to native hPI via disulfide reshuffling. Most of the trimers and larger aggregates, however, could not be converted to hPI in 24 hours, unless they were exposed to a high concentration of a strong reducing reagent, which also caused unfolding of the native hPI. Understanding the competition of the aggregation reactions and the productive folding reactions enabled us to develop effective protocols to optimize the dissolution procedure, the composition of the tandem folding agents, and the timing for adding the strong reducing agent (or temporal programming). Through preliminary optimization, the new method gave an average folding yield of 73% for folding 1 g/L hPSS. The yield for conventional folding using only one redox pair, cysteine/cystine, is 45-60% for 1 g/L hPSS.

Figure 1E:
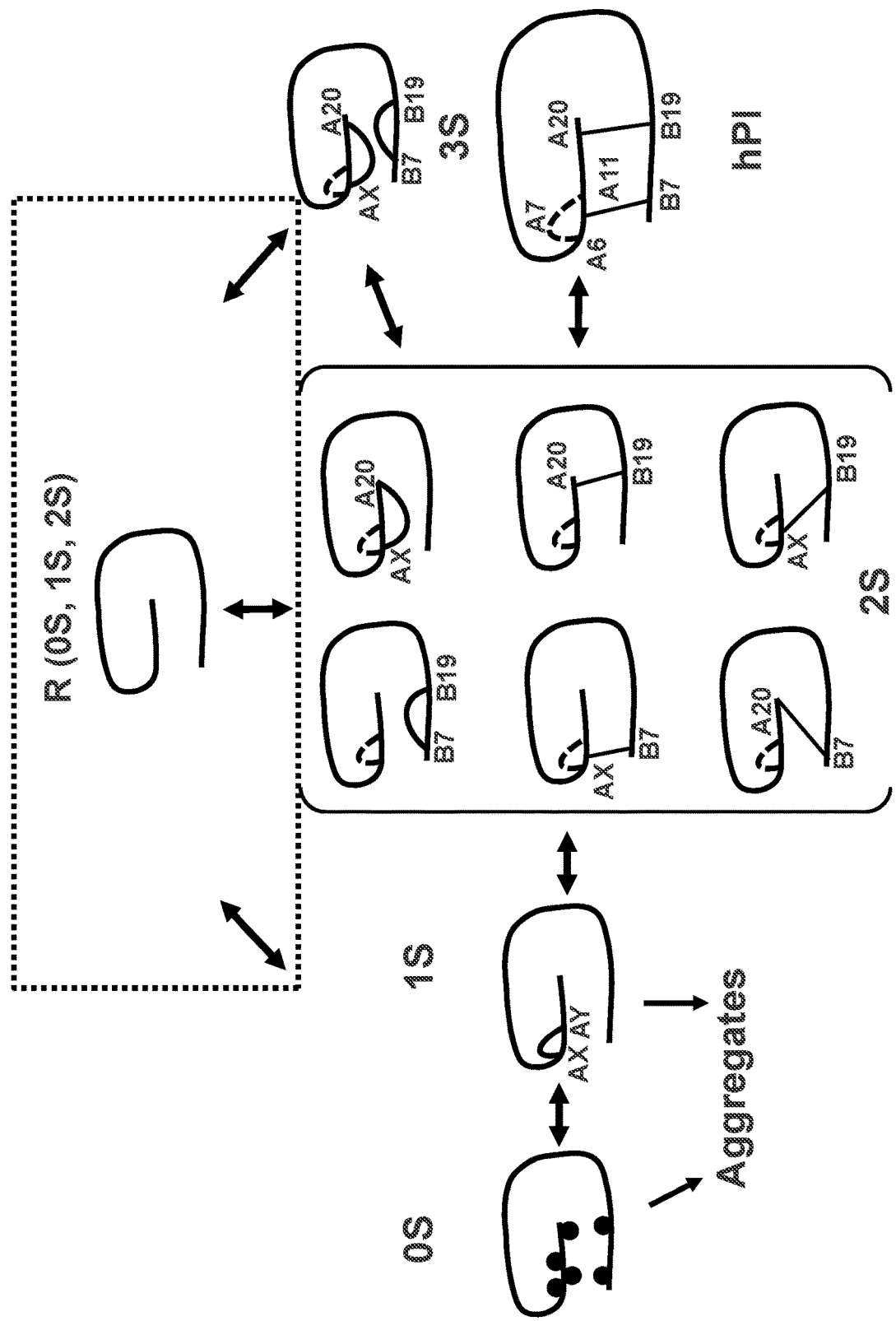
FIG. 1E depicts the disulfide formation pathways from MR-KPB-hPSS (hPSS) to MR-KPB-hPI (hPI). In the presence of excess cysteine, MR-KPB-hPI and folding intermediates are reduced to reduced species "R" or misfolded monomers as indicated by the dashed box.

In summary, the physical (non-covalent) factors found to affect folding yield can include (1) thawing conditions of frozen hPSS, (2) hPSS dilution conditions (pH, temperature, mixing speed, and mixing time), (3) salt concentrations in the hPSS solution, and (4) state of cysteine addition (added as a solid or as a solution). The reaction (covalent) factors affecting yield can include (1) the types of the reducing agent (cysteine/cystine, GSH/GSSG), (2) the concentrations of the redox agents, (3) type of second strong reducing agent (DTT, TCEP), and (4) timing of addition of the second strong reducing agent. In the pro-insulin case, the timing of the second reducing agent must be added after the formation of the first native disulfide bond (A6-A11), between 5 and 10 min after the initiation of folding. Any intermediates without the A6-A11 native bond (denoted as the misfolded in FIG. 15C) could not be converted to hPI. Apparently, disulfide reshuffling can correct the mistakes in forming the second and the third disulfide bonds (FIG. 1E), but not the intermediates without the native bond of A6-A11. The dimers, trimers and larger aggregates form during the first hour of folding (FIG. 16) and these reactions are mostly irreversible under the favorable folding conditions, resulting in significant yield loss. For these reasons, the second strong reducing agent cannot be added too late (after the first hour). Adding the second reducing agent too early (before initiation of folding or 5 min after the initiation) can break up the large aggregates into dimers and trimer (FIG. 16), but also generates misfolded intermediates (without the A6-A11 native bond), which cannot be refolded in 24 hours (FIG. 15C). A strong reducing agent at a higher concentration can break the dimers, trimers and larger aggregates, but it also causes unfolding of the correctly folded protein. For these reasons, addition of a strong reducing agent at an appropriate concentration at 10 min gave the best yield (~73%, FIG. 15A).

Cysteine-Containing Proteins

Methods provided herein can be used to refold a variety of cysteine-containing proteins. Generally, the refolding process is considerably slower for cysteine-containing proteins due to the formation of non-native disulfide bonds. The therapeutic proteins containing cysteine residues generally require the formation of proper disulfide bonds to maintain their native structures and stability. In various embodiments, the methods provided herein can provide for refolding of cysteine-containing proteins with higher yield of the native protein form.

The misfolding and slow folding rate of cysteine-containing proteins is generally exacerbated by an increasing number of cysteine residues in the protein. As the number of cysteines increases, the number of nonnative species can increase factorially. In some aspects, the methods provided herein are particularly useful for cysteine-rich proteins, e.g. proteins having 4, 5, 6, 7, 8, 9, 10, or more cysteine residues.

The cysteine-containing protein can include an enzyme, an antibody, an antigen, a hormones, or a cytokine. The protein can be an interleukin or a growth factor. The protein can be a recombinant protein, e.g. isolated from an *Escherichia coli* expression system. The recombinant protein can be an inclusion body from the *Escherichia coli* expression system that has been solubilized by the addition of chemical denaturant. In various aspects, the cysteine-containing protein is insulin, an insulin analogue, a proinsulin, or a proinsulin analogue.

The term "insulin" as used herein, refers to human insulin, whose amino acid sequence and special structure are well-known. Human insulin is comprised of a twenty-one amino acid A-chain and a thirty-amino acid B-chain which are cross-linked by disulfide bonds. A properly cross-linked insulin contains three disulfide bridges: one between position 7 of the A-chain and position 7 of the B-chain, a second between position 20 of the A-chain and position 19 of the B-chain, and a third between positions 6 and 11 of the A-chain.

The term "insulin analog" means proteins that have an A-chain and a B-chain that have substantially the same amino acid sequences as the A-chain and B-chain of human insulin, respectively, but differ from the A-chain and B-chain of human insulin by having one or more amino acid deletions, one or more amino acid replacements, and/or one or more amino acid additions that do not destroy the insulin activity of the insulin analog. "Animal insulins" are insulin analogs. Four such animal insulins are rabbit, pork, beef, and sheep insulin. Another type of insulin analog, "monomeric insulin analog" is well-known in the art. Monomeric insulin analogs are structurally very similar to human insulin, and have activity similar or equal to human insulin, but have one or more amino acid deletions, replacements or additions that tend to disrupt the contacts involved in dimerization and hexamerization which results in their greater tendency to dissociate to less aggregated states. Monomeric insulin analogs are rapid-acting analogs of human insulin, and are disclosed, for example, in Chance, R. E., et al., U.S. Pat. No. 5,514,646, 7 May 1996; Brems, D. N., et al. Protein Engineering, 5:527-533 (1992); Brange, J. J. V., et al., EPO publication No. 214,826, published 18 Mar. 1987; Brange, J. J. V., et al., U.S. Pat. No. 5,618,913, 8 Apr. 1997; and Brange, J., et al., Current Opinion in Structural Biology 1:934-940 (1991).

The term "proinsulin" means a single-chain peptide molecule that is a precursor of insulin or an insulin analog. Proinsulin may be converted to insulin or to an insulin analog by chemical or, preferably, enzyme-catalyzed reactions. In proinsulin, proper disulfide bonds are formed as described herein. Proinsulin comprises insulin or an insulin analog and a connecting bond or a connecting peptide. A connecting peptide has between 1 and about 35 amino acids. The connecting bond or connecting peptide connects to a terminal amino acid of the A-chain and to a terminal amino acid of the B-chain by an α-amide bond or by two α-amide bonds, respectively. Preferably, none of the amino acids in the connecting peptide is cysteine. Preferably, the C-terminal amino acid of the connecting peptide is Lys or Arg. Proinsulin may have the formula X-B-C-A-Y or may have the formula X-A-C-B-Y, wherein X is hydrogen or is a peptide of from 1 to about 100 amino acids that has either Lys or Arg at its C-terminal amino acid, Y is hydroxy, or is a peptide of from 1 to about 100 amino acids that has either Lys or Arg at its N-terminal amino acid, A is the A-chain of insulin or the A-chain of an insulin analog, C is a peptide of from 1 to about 35 amino acids, none of which is cysteine, wherein the C-terminal amino acid is Lys or Arg, and B is the B-chain of insulin or the B-chain of an insulin analog.

The cysteine-containing protein can be present at an elevated concentration. In various aspects, the concentration of the cysteine-containing protein in the solution prior to initiating the refolding is about 0.1 g/L to about 3 g/L, about 0.1 g/L to 2 g/L, about 0.1 g/L to 1 g/L, about 0.3 g/L to 1 g/L, about 0.3 g/L to 2 g/L, about 0.3 g/L to 3 g/L, about 0.5 g/L to 3 g/L, about 0.5 g/L to 2 g/L, about 0.5 g/l to 1.5 g/L, or about 0.8 g/L to 1.5 g/L.

Dissolution of Cysteine-Containing Proteins

In various aspects, the methods provided herein include dissolution of cysteine-containing proteins to produce a solubilized cysteine-containing protein. The solubilized protein can have an increased number of denatured/extended monomers as compared to the solution of the cysteine-containing protein prior to the dissolution.

The dissolution can include dissolution of the cysteine-containing protein at an alkaline pH to form the solubilized cysteine-containing protein. The alkaline pH can be any alkaline pH sufficient to increase the concentration of the denatured/extended monomers as compared to the concentration of the denatured/extended monomers in the otherwise same solution except at a pH of about 11, 10.9, 10.8, 10.7, 10.6, 10.5, 10.0 or less. The alkaline pH can, in various embodiments, be about 11.2 to 12.5, about 11.5 to 12.5, about 11.5 to 12.2, about 11.7 to 12.2, or about 11.8. In various aspects, the alkaline pH is such that the pH of the solvent does not drop to cause increased aggregation upon the initiation of folding.

The dissolution can include dissolution at a temperature that is optimized to increase the concentration of the denatured/extended monomers in the solution. In various aspects, the temperature is about 2° C., about 3° C., about 4° C., about, 5° C., about, 6° C., about, 7° C., about, 8° C., about 2° C. to 12° C., about 2° C. to 10° C., about 4 to 10° C., or about 4° C. to 8° C.

In various aspects, the hydrodynamic radius of the cysteine-containing protein, as determined by fluorescence correlation spectroscopy, is within about 35%, 30%, 25%, 20%, or 15% of the cysteine-containing protein's equivalent spherical radius.

Refolding a Solubilized Cysteine-Containing Protein

In various aspects, methods of refolding a solubilized cysteine-containing protein to its native form are provided. The methods can result in increased yield of the native protein form upon folding. The methods can include a tandem folding process, whereby two different reducing agents with different reduction strengths are used to control the rate of folding and the formation of aggregates to increase the native protein yield. In various aspects, the methods can include adding a reversible reducing agent to a solution containing the solubilized cysteine-containing protein initiate folding of the cysteine-containing protein, and adding an irreversible reducing agent to the solution at a time after the initiation of folding to breakdown aggregates of the cysteine-containing protein.

A variety of reversible reducing agents are known to induce protein folding. In various aspects, the reversible folding agents include cysteine, cystine, cysteamine, cystamine, beta-mercaptoethanol, glutathione-reduced, glutathione-oxidized, derivatives thereof, and combinations thereof. The reversible folding agent can be added at a ratio of [reversible reducing agent]:[thiols in the cysteine-containing protein] of about 2:1 to 5:1, about 3:1 to 5:1, about 3:1 to 4:1, or about 7:2.

The irreversible reducing agent is added at a time after the initiation of folding, i.e. at a time after the addition of the reversible reducing agent. In various aspects, at least some of the cysteine-containing protein forms a dimer, and the time after the initiation of folding is when the concentration of the dimer in the solution is about 3 mol % to 15 mol %, about 5 mol % to 15 mol %, about 7 mol % to 15 mol %, about 10 mol % to 15 mol %, about 10 mol % to 12 mol %, about 7 mol % to 12 mol %, about 5 mol % to 12 mol %, or about 3 mol % to 12 mol % based upon the concentration of the cysteine-containing protein.

The irreversible reducing agent is added at a time after the initiation of folding, i.e. at a time after the addition of the reversible reducing agent. In various aspects, at least some of the cysteine-containing protein forms a dimer, and the time after the initiation of folding is when the concentration of the dimer in the solution is about 1.5 to 5.0 times, about 1.5 to 4.0, times, about 1.5 to 3.0 times, about 2.0 to 3.0 times, about 2.0 to 4.0 times, or about 2.0 to 5.0 times the concentration of the dimer in the solution prior to the addition of the reversible reducing agent.

The irreversible reducing agent is added at a time after the initiation of folding, i.e. at a time after the addition of the reversible reducing agent. In various aspects, the time after the initiation of folding is about 2.5 minutes to 25 minutes, about 5 minutes to 25 minutes, about 10 minutes to 25 minutes, about 10 minutes to 20 minutes, or about 10 minutes to 15 minutes. In various aspects, the refolding process takes place for about 5 hours, about 10 hours, about 15 hours, about 24 hours, or more.

In various aspects, the pH of the solution is such that the addition of the reversible reducing agent does not reduce the pH of the solution below about 10.5, about 10.6, about 10.7, about 10.8, or about 10.9. In some embodiments, the pH of the solution after the addition of the reversible reducing agent is about 10.75 to about 10.85.

In some aspects, the reversible reducing agent is cysteine-HCl. The reversible reducing agent can be cysteine-HCl dissolved to about 200 mM to about 900 mM at about 4° C. to 8° C. and acidic pH.

The methods provided herein can be used to refold a variety of proteins with high yields. In various aspects, the yield of the native form of the cysteine-containing protein is higher than the yield of the native form for the same cysteine-containing protein refolded under the otherwise same conditions except without the addition of the irreversible reducing agent. In some aspects, the yield of the native form of the cysteine-containing protein is about 20%, 30%, 40%, or 50% more than the yield of the native form for the same cysteine-containing protein refolded under the otherwise same conditions except without the addition of the irreversible reducing agent.

In some aspects, the yield of the native form of the cysteine-containing protein is higher than yield of the native form for the same cysteine-containing protein refolded under the otherwise same conditions except where the irreversible reducing agent is added at the same time as the reversible reducing agent. In some aspects, the yield of the native form of the cysteine-containing protein is about 20%, 30%, 40%, or 50% more than the yield of the native form for the same cysteine-containing protein refolded under the otherwise same conditions except where the irreversible reducing agent is added at the same time as the reversible reducing agent.

In certain aspects, the yield of the native form of the cysteine-containing protein is about 50 mol % to 90 mol %, about 60 mol % to 90 mol %, about 70 mol % to 90 mol %, 70 mol % to 80 mol %, about 60 mol % to 80 mol %, or about 65 mol % to 75 mol % based upon the concentration of the cysteine-containing protein.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Irreversible folding agents can include dithiothreitol (DTT), tris(2-carboxyethyl) phosphine (TCEP), thioglycolic acid, derivatives thereof, or combinations thereof. The irreversible reducing agent can have a redox potential of about −0.29 V to −0.35V about, −0.3 V to −0.35V, or about −0.29 V to −0.32 V at a pH above 7.0. In some aspects, the irreversible reducing agent has a redox equilibrium constant of about $10^3$, $10^4$, $10^5$, or more. The irreversible reducing agent can be added at a ratio of [irreversible reducing agent]:[thiols in the cysteine-containing protein] of about 0.3:1 to about 1:1, about 0.5:1 to about 1:1, about 0.6:1 to about 1:1, about 0.6:1 to about 0.8:1, about 0.5:1 to about 0.8:1, about 0.3:1 to about 0.8:1, or about 0.3:1 to about 0.6:1. In various aspects, the irreversible reducing agent can be added at a ratio of [irreversible reducing agent]:[cysteine groups involved in nonnative disulfide bonds] of about 1:1 or less.

Materials

Crude solutions of MR-KPB-hPSS and purified solutions of KPB-hPI were kindly provided by Eli Lilly & Co. and were stored at −20° C. L-cysteine hydrochloride (>98%), tris(2-carboxyethyl) phosphine hydrochloride (>98%), and 6-(p-toluidino)-2-naphthalenesulfonic acid sodium salt (>98%) were purchased from Sigma-Aldrich (St. Louis, Mo.). HPLC-grade acetonitrile and (99%) trifluoroacetic acid were purchased from ACROS (Morris Plains, N.J.). Glycine was purchased from Mallinckrodt Baker (Phillipsburg, N.J.). Dithiothreitol (>99%) was purchased from Gold Biotechnology (St. Louis, Mo.). An 8-well Lab-tek Nunc chambered coverglass was used for FCS experiments.

Methods

Fluorescence Correlation Spectroscopy

Figure 2:
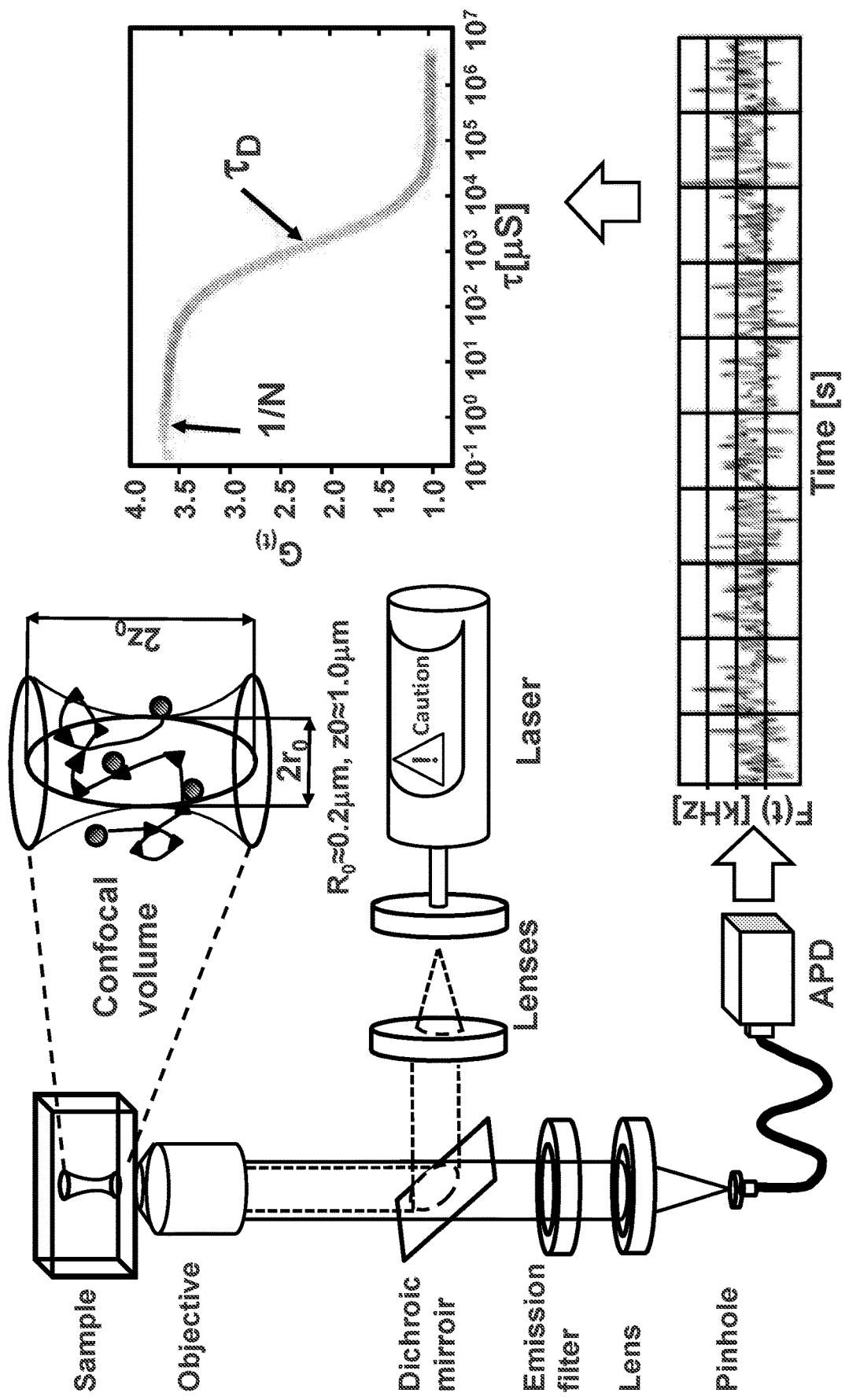
FIG. 2 is a diagram of an exemplary equipment and method for fluorescence correlation microscopy.

Single-photon fluorescence fluctuation measurements were conducted with an Alba Fluorescence Correlation Spectrometer. A beam alignment was performed before all experiments; coverslips with 60 µL samples were used. Laser excitation at 446 nm, 68% power, and pinhole size 100 were used for all measurements. FCS measurements occurred at room temperature and lasted 100 s with data collected at 100 k Hz. The FCS set-up with confocal microscopy is shown in FIG. 2 (Koynov & Butt, 2012).

hPSS Dissolution and Folding: Method 1
1. Thaw MR-KPB-hPSS in 4° C. cold room overnight.
2. Dilute stock solution to 1 g/L with chilled (4° C.) DI water to a final folding volume of 400 mL.
3. In an ice bath, adjust the pH of the broth to pH 11.8 with 4° C. 10% (v/v) NaOH.
4. Stir hPSS broth at ~200 rpm for 30 min with stir plate in cold room.
5. Add solid cysteine-HCl to hPSS broth in a [Cys]:[thiol] ratio of 3.5.
6. In an ice bath, initiate the reaction by adding 4° C. 10% (v/v) NaOH to adjust the pH to 10.8.
7. Transfer broth to cold room for folding reaction. Stir hPSS broth at ~200 rpm with stir plate for 24 hr.
8. Take 1 mL samples at recorded time intervals. Quench the samples with an equal volume of 0.1 M glycine (pH 2).
9. Store quenched samples in −20° C. freezer until HPLC and FCS measurements can be taken.
10. Thaw sample vials in cold room for 30 min prior to assay.

hPSS Dissolution and Folding: Method 2
1. Thaw MR-KPB-hPSS in 4° C. cold room overnight.
2. Dilute stock solution to 1 g/L with chilled (4° C.) DI water to a final folding volume of 400 mL.
3. In an ice bath, adjust the pH of the broth to pH 11.8 with 4° C. 10% (v/v) NaOH.
4. Stir hPSS broth at ~200 rpm for 30 min with stir plate in cold room.
6. Adjust the pH of the cysteine-HCl stock solution to pH 1.5 using 10% (v/v) NaOH.
7. Add cysteine-HCl stock solution (~800 mM) to hPSS broth in a [Cys]:[thiol] ratio of 3.5.
6. In an ice bath, initiate the reaction by adding 4° C. 10% (v/v) NaOH to adjust the pH to 10.8.
7. Transfer broth to cold room and stir at ~200 rpm with stir plate for 10 min
8. After 10 min of folding, add TCEP-HCl stock solution (~150 mM) to hPSS broth in a [TCEP]:[thiol] ratio of 2:3.
9. In an ice bath, readjust the pH of the folding broth to pH 10.8 with 4° C. 10% (v/v) NaOH.
10. Transfer broth to cold room for folding reaction. Stir hPSS broth at ~200 rpm with stir plate for 24 hr.
11. Take 1 mL samples at recorded time intervals. Quench the samples with an equal volume of 0.1 M glycine (pH 2).
12. Store quenched samples in −20° C. freezer until HPLC and FCS measurements can be taken.
13. Thaw sample vials in cold room for 30 min prior to assay.

Size Exclusion HPLC Analysis
System Agilent 1100 HPLC
Column: Waters Insulin HMWP. 7.8 mm×300 mm
Mobile Phase: Mobile Phase: 65% (v/v) 1.0 g/L L-arginine solution, 20%
(v/v) Acetonitrile, 15% (v/v) glacial acetic acid
Injection: Injection: 100 µL per sample
Detector at 276 nm
Operating Conditions: Flow rate: 0.5 mL/min
Column temperature: 25° C.
Sample chamber temperature: 20° C.
Description: SEC separates folding intermediates by size. The approximate retention times are: 12.8 min for large aggregates, 13.3-14.6 min for dimers/trimers, 16 min for monomeric folding intermediates, 17 min for native hPI, and 18 min for misfolded proinsulin. In calculating the hPI yield from the SEC chromatogram, extinction coefficients of dimers, trimers, and large aggregates are assumed to be 2, 3, and 5 times that of monomers, respectively. Integrated peak areas were found from vertical cuts, as slanted cuts contributed only a few percent to the peak areas.

Reversed-Phase HPLC Analysis

Column: Agilent Zorbax 300SB-C8. 4.6 mm×150 mm, 5 μm Part No. 883995-906

Mobile Phase: Mobile Phase A: 0.15% (v/v) trifluoroacetic acid in water

Mobile Phase B: Acetonitrile

Regeneration: 60% mobile phase B

Re-equilibration: 30% mobile phase B

Injection: Injection: 25 μL per sample. Detector at 214 nm

Elution: Linear gradient of Mobile Phase B from 30-40% over 60 minutes

Regeneration: 15-minute regeneration

Re-equilibration: 10-minute re-equilibration

Operating Conditions: System: Agilent 1100 HPLC in FRNY1006

Flow rate: 0.5 mL/min

Column temperature: 35° C., Sample chamber temperature:

20° C.

Description The retention time of native hPI is ~14 min; this peak consists of 3 shoulders that represent MR-KPB-hPI and two related substances: native proinsulin without methionine in the leader sequence (R-KPB-hPI) and native proinsulin with an oxidized methionine M(O)R-KPB-hPI. In calculating the yield, the area under the MR-KPB-hPI, R-KPB-hPI, and M(O)R-KPB-hPI peaks is correlated to concentration using a purified MR-KPB-hPI standard (also containing R—KPBhPI and M(O)R-KPB-hPI peaks).

Results and Discussion hPSS Dissolution

Fluorescence Characterization

A hydrophobic probe, 6,P-toluidinylnaphthalene-2-sulfonate (TNS), was identified as a potential fluorescent probe. In an aqueous environment, TNS does not generate a significant fluorescent signal. Upon interacting with hydrophobic residues, fluorescence is observed. To determine the optimal TNS:hPSS ratio, steady-state fluorescence measurements were conducted at 350 nm and 440 nm excitation to generate the emission spectra.

A Job plot is a method used to evaluate the stoichiometry of binding interactions. In a Job plot, the total concentration (probe+ligand) is constant, with the molar fraction of the probe plotted on the x-axis and signal intensity plotted on the y axis. When used to evaluate the binding stoichiometry of TNS to a protein, the maximum intensity of a Job plot indicates the number of hydrophobic binding sites on the protein (Buccigross, Bedell, & SudingMoster, 1996). Shown in FIG. 3, a Job Plot was generated by plotting the maximum fluorescence emission as a function of TNS mole fraction at a constant total concentration ([TNS]+[hPSS]). The maximum of the plot indicates the optimal TNS:hPSS ratio. At a 350 nm excitation, the optimal TNS:hPSS molar ratio is 1:2. At an excitation of 440 nm, TNS does not contribute significantly to the fluorescence, however a fluorescence signal is still observed.

The results of the steady-state fluorescence measurements indicate that, at the excitation wavelength used for FCS (~440 nm), the intrinsic fluorescence of the hPSS broth is too high to be neglected. Because the intrinsic fluorescence signal cannot be decoupled from the TNS interaction signal, further studies were conducted to determine the location of the intrinsic pigment in the hPSS broth and whether the pigment could be removed.

In an attempt to remove the pigment from the hPSS broth, a batch test was conducted with activated carbon. The pigment was found to persist through the test, indicating that the pigment is likely coupled to proteins in solution.

The hPSS broth was dialyzed in a membrane with MWCO=8000 Da, which is slightly lower than the molecular weight of hPSS (9400 Da). The pigment was not removed through dialysis, confirming that the intrinsic fluorescence was coupled to the protein. The SDS-PAGE analysis shows that hPSS is the only protein in the broth that could be coupled to the pigment (data not shown).

Both hPSS and hPI were found to have an intrinsic signal. To avoid convoluting the FCS measurements with multiple fluorescent dyes, the intrinsic fluorescence of hPI and hPSS were used for all FCS measurements.

Identify Relevant Non-Covalent Interactions

The oxidative sulfitolysis of proinsulin to hPSS results in denatured peptides that cannot form disulfide bonds without the addition of a reducing agent; however, SEC and FCS data suggest that hPSS peptides flocculate (form reversible, non-covalently attached aggregates) before the initiation of folding. The potential mechanisms for protein-protein interactions are electrostatic and hydrophobic interactions. FCS was used to characterize these interactions and their impacts to hPSS flocculation before folding.

Figure 4:
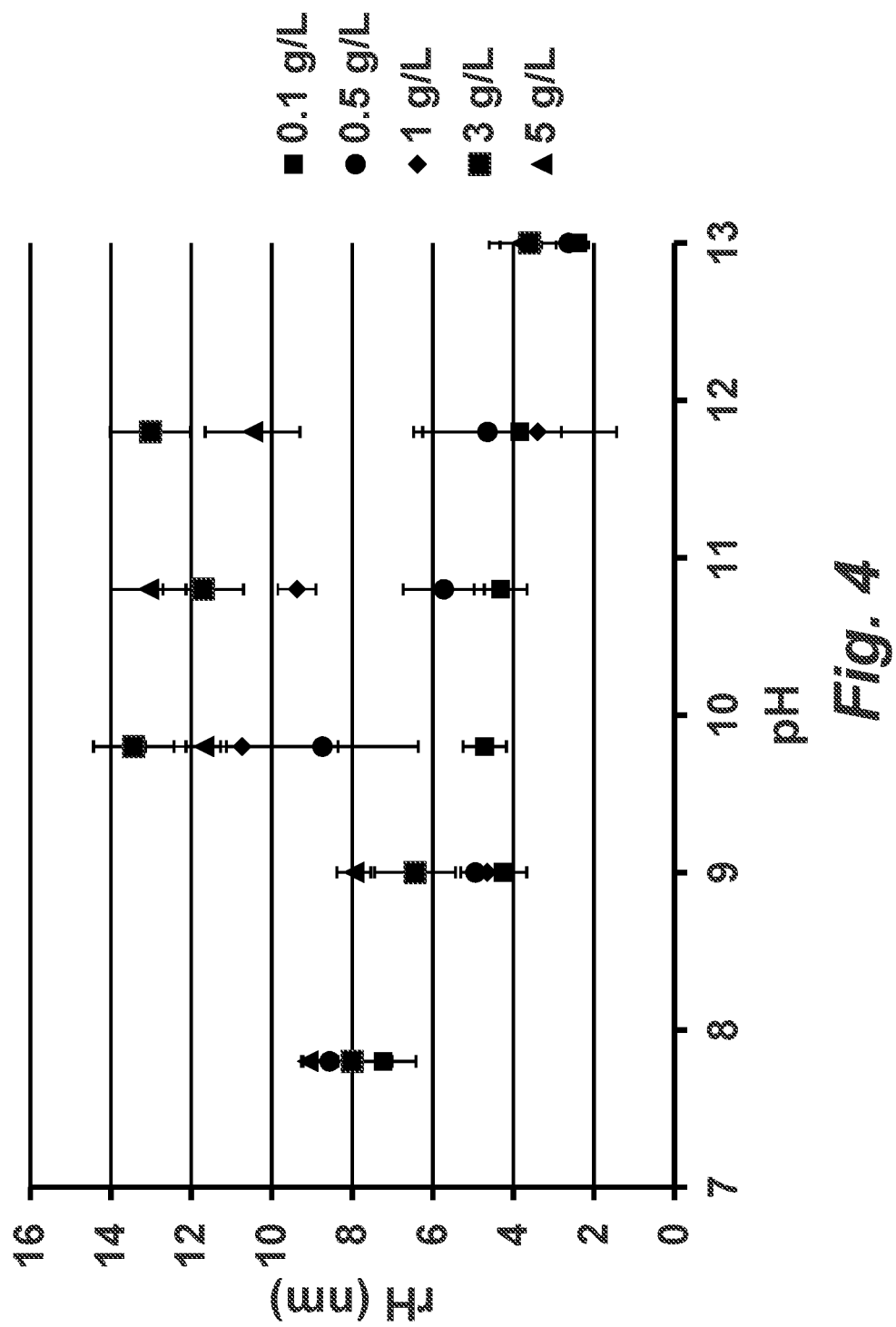
FIG. 4 is a graph of the hydrodynamic radius of hPSS as a function of pH for various hPSS concentrations from 0.1 g/L (filled squares) to 5 g/L (open triangles).
Figure 5:
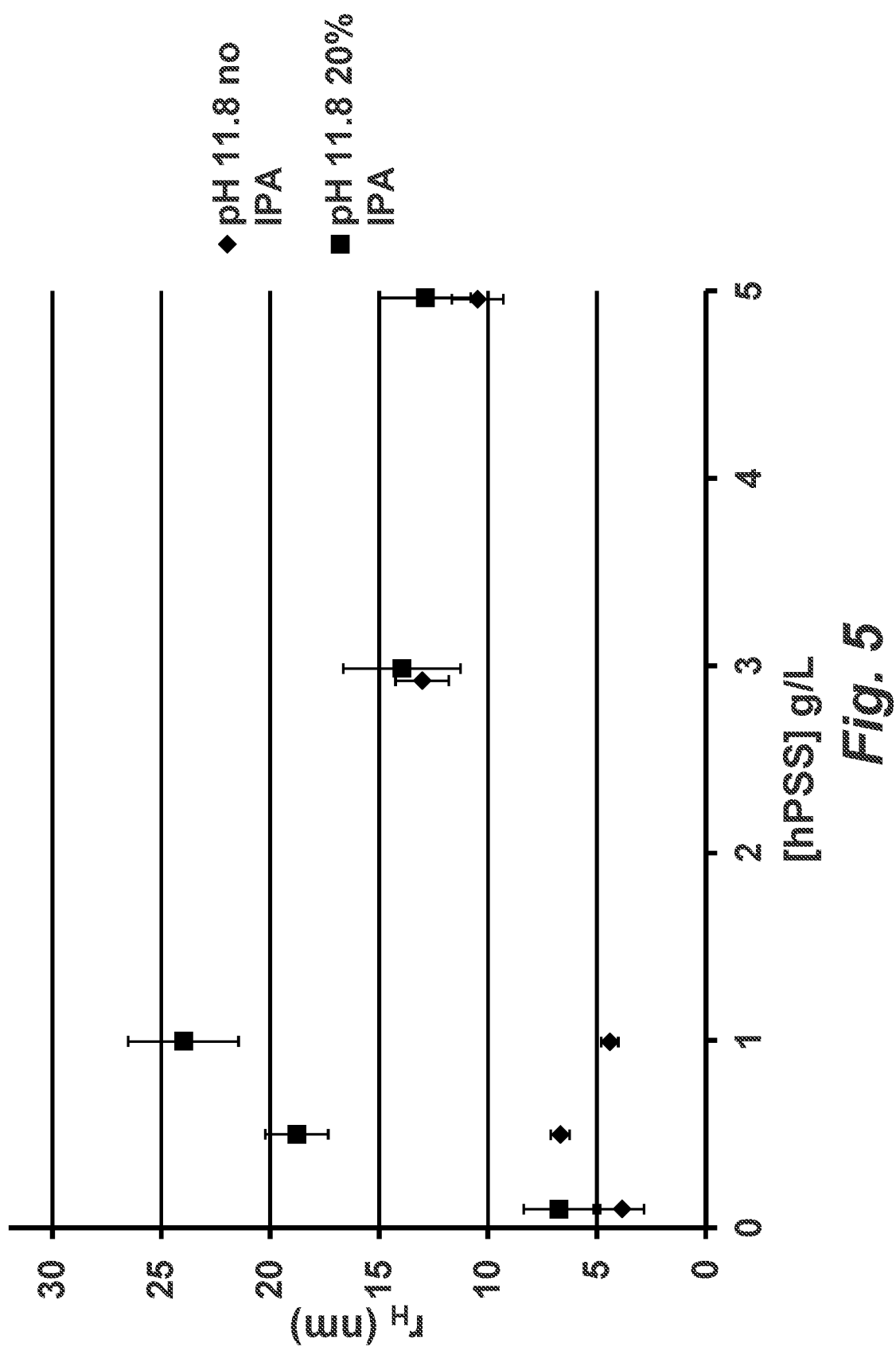
FIG. 5 is a graph of the hydrodynamic radius of hPSS in deionized water (DI) water without (open diamonds) and with (closed squares) isopropyl alcohol (IPA) at pH 11.8 as a function of the concentration of hPSS (g/L).

To determine the contribution of hydrogen bonding to hPSS flocculation, 2-propanol (IPA) was added to pH 11.8 hPSS broth. As seen in FIG. 5, 20% (v/v) IPA increased the hydrodynamic radius of hPSS. In 50% (v/v) IPA, hPSS formed precipitates (data not shown). Addition of IPA increased the $r_H$ of hPSS, likely due to the disruption of hydrogen bonding between hPSS and the buffer matrix. Further addition of alcohols is not expected to mediate flocculation. To examine the effect of electrostatic interactions on hydrodynamic radius, NaOH and HCl were added to the hPSS broth, thus varying the pH. Shown in FIG. 4, the radius of hPSS decreases as pH increases at low concentrations. At high concentrations, the $r_H$ of hPSS is highest and the response of the aggregate state to pH is less apparent At low pH values, there is high variation in the aggregate state of hPSS, however at pH 13 the hPSS appears to be primarily in monomeric form as the $r_H$ is between 2.4 nm and 3.8 nm at this pH, regardless of concentration.

Figure 6A:
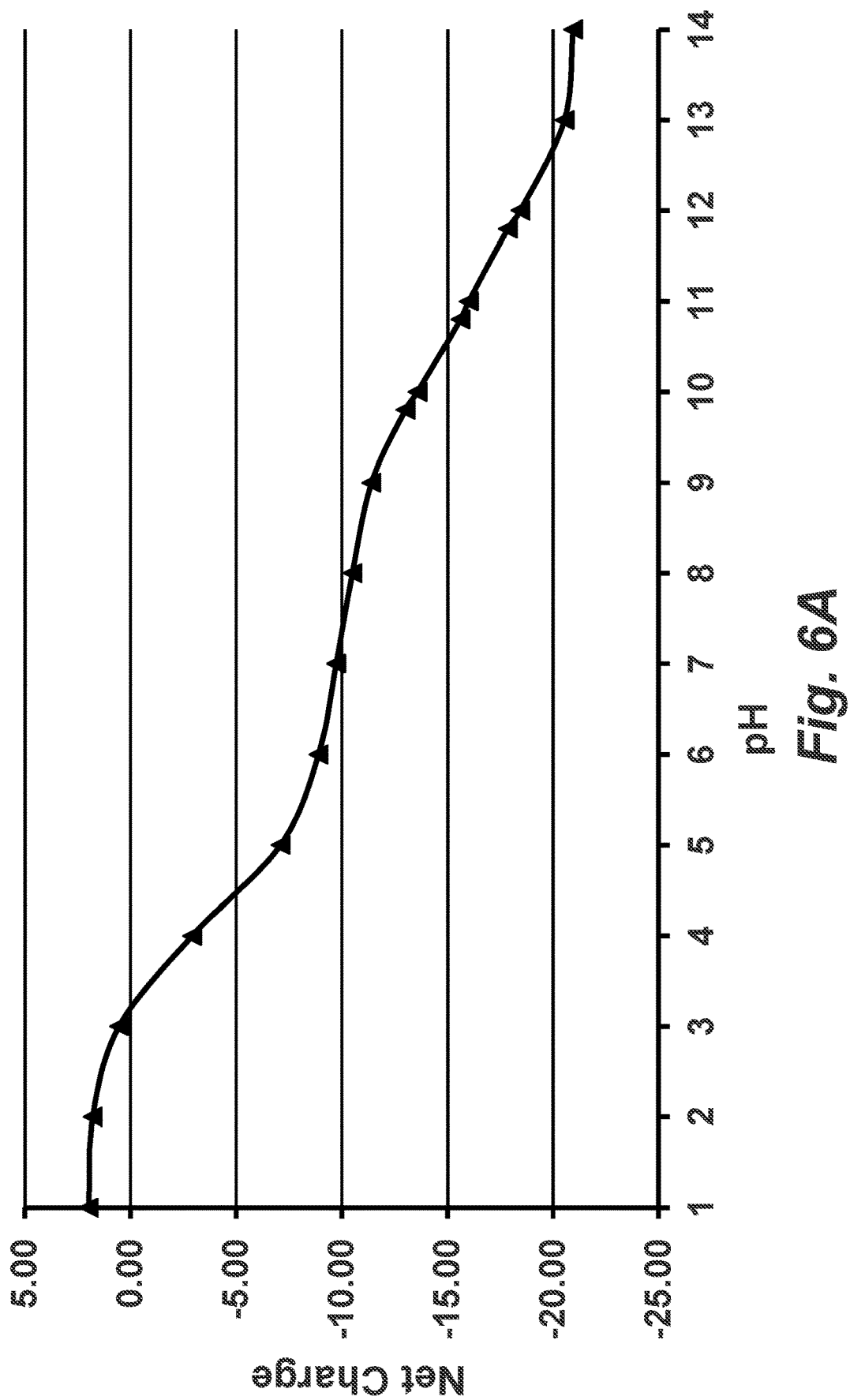
FIGS. 6A-6B are graphs of the predicted net (FIG. 6A) and absolute charge (FIG. 6B) of hPSS using $H^+$ concentration and $pK_A$ computation.
Figure 6B:
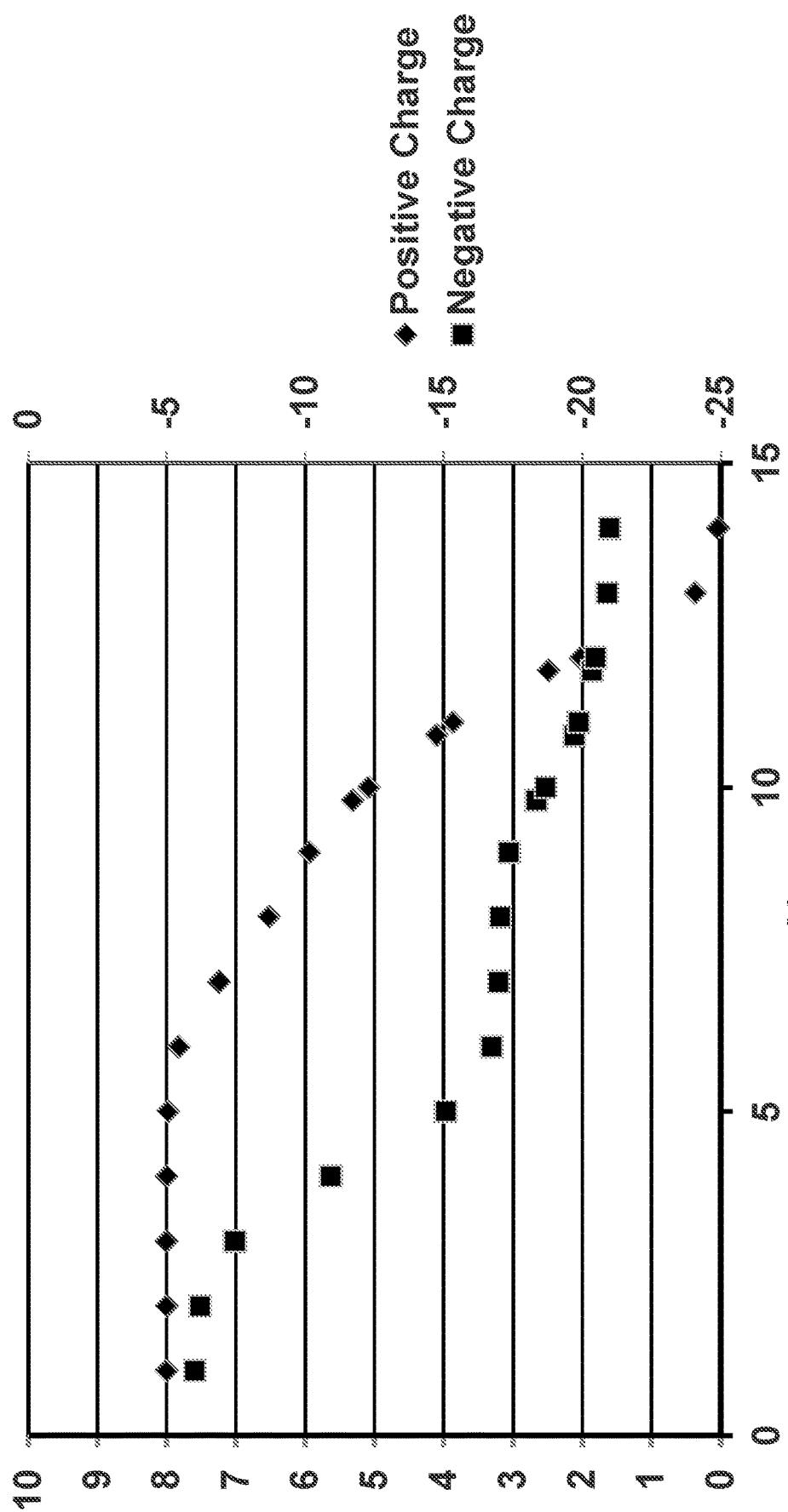
Figure 7:
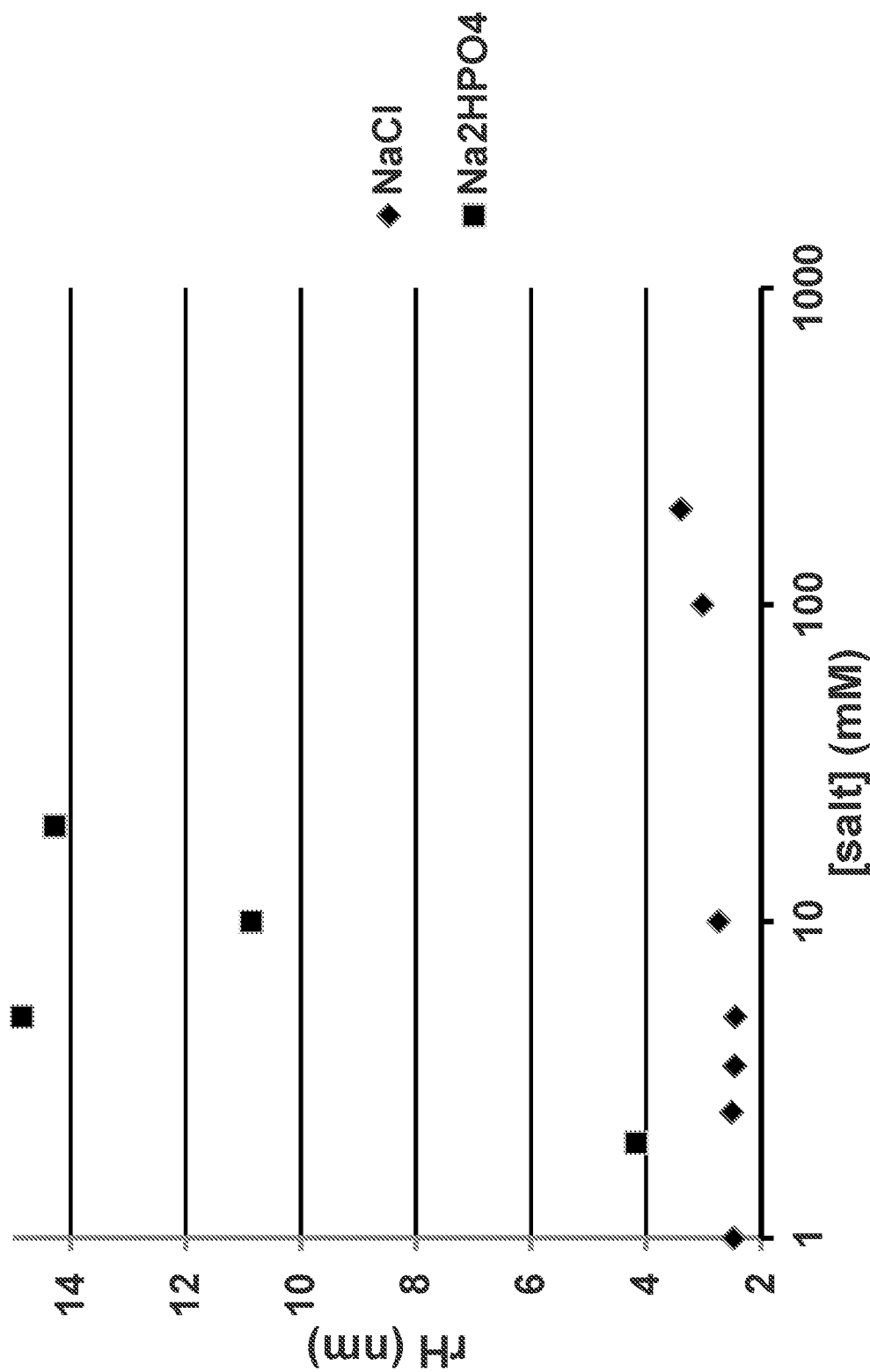
FIG. 7 is a graph of the hydrodynamic radius of hPSS for a 1 g/L hPSS solution as a function of salt concentration for NaCl (closed diamonds) and $Na_2HPO_4$ (closed squares) at a pH of 11.8.

The radius of hPI in monomeric form was measured by FCS to be ~2.4 nm, which is consistent with the dimensions of hPI (dimensions give an equivalent spherical radius of 2.8 nm) and is similar to the radius of hPSS. The charge distribution of hPSS is predicted in FIG. 6A. Between pH 7.8 and 13, four negative charges are gained, while seven positive charges are lost. At pH 13, there are no positively charged groups. The decrease in hPSS aggregation at high pH is therefore likely due to the elimination of positively charged residues.

The effect of electrostatic interactions on hPSS flocculation was further investigated with the addition of salts. The dissolution of hPSS in 1 mM to 200 mM NaCl at pH 11.8 did not cause or mitigate aggregation. In $Na_2HPO_4$ at pH 11.8, hPSS formed flocs at and above 5 mM $Na_2HPO_4$.

Aggregation and Misfoldinq of Proinsulin During Folding

A summary of all foldings is shown in Table 1, while the optimal dissolution and folding conditions are shown in Table 2. Higher yields were obtained from the newer hPSS lot (MR-KPB-hPSS, KPB TFF1 Retentate, Lot# A706083, Prepared 13 Jan. 2010) than from the older lot (MR-KPB-hPSS, KPB TFF1 Retentate, Lot# A489010, Prepared 24

Apr. 2008). This is potentially due to protein denaturation during storage and the older lots encountering more freeze-thaw cycles.

The dissolution pH was found to have a significant effect on folding yield. When the dissolution pH was too high or too low, misfolding occurred; dissolution at pH 11.8 for 30 min was optimal in reducing misfolding. The addition of solid cysteine-HCl resulted in uncontrolled flocculation of pH; adding cysteine-HCl as a pH 1.5 buffer from an 800 mM stock solution resulted in better mixing conditions and higher yields.

The temperature of DI water used to dilute the concentrated hPSS stock solution also affected folding yields. Diluting the hPSS with room temperature water resulted in poor dissolution, while diluting the hPSS with chilled DI water dissolved the hPSS to a monomeric form. Dissolution of the stock solution at pH 11.8 in 10 mM $Na_2HPO_4$ was poor, and subsequent folding resulted in high yield loss to aggregation. The addition of strong reducing agents resulted in increased yields; when TCEP or DTT were added after 10 min of folding, the amount of yield lost to aggregation was reduced.

TABLE 1

Summary of all folding reactions

| Run | Yield (%) | hPSS concentration (g/L) | Cysteine addition | pH of cys addition | Dilution temp (° C.) | Dissolution pH | time of dissolution (min) | Date | Batch Date* |
|---|---|---|---|---|---|---|---|---|---|
| 1 | <5 | 1 | Buffer | 13 | 5 | 13 | 300 | Oct. 20, 2013 | New |
| 2 | 35 | 1 | Buffer | 8.5 | 5 | 8.5 | 300 | Oct. 28, 2013 | New |
| 3 | <5 | 1 | Buffer | 13 | 5 | 13 | 300 | Oct. 30, 2013 | New |
| 4 | 67 | 0.2 | Buffer | 11.8 | 5 | 11.8 | 30 | Nov. 16, 2013 | New |
| 5 | 25 | 1 | Buffer | 11.8 | 5 | | 30 | Jan. 4, 2014 | New |
| 6 | 67 | 1 | Buffer | 11.8 | 5 | 13 | 30 | Jan. 23, 2014 | New |
| 7 | 41 | 0.5 | Buffer | 11.8 | 20 | 11.8 | 90 | Jan. 31, 2014 | Old |
| 8 | 27 | 0.5 | Buffer | 11.8 | 5 | 11.8 | 90 | Feb. 7, 2014 | Old |
| 9 | 41 | 0.5 | Buffer | 11.8 | 20 | 11.8 | 90 | Feb. 14, 2014 | New |
| 10 (10 mM PBS) | 35 | 1 | Buffer | 11.8 | 5 | 11.8 | 90 | Feb. 20, 2014 | New |
| 11 (0.05 mM TCEP) | 55 | 1 | Buffer | 11.8 | 5 | 11.8 | 30 | Mar. 6, 2014 | Old |
| 12 (0.1 mM TCEP) | 59 | 1 | Buffer | 11.8 | 5 | 11.8 | 30 | Mar. 14, 2014 | Old |
| 13 (0.2 mM TCEP) | 64 | 1 | Buffer | 11.8 | 5 | 11.8 | 30 | Mar. 14, 2013 | Old |
| 14 (0.4 mM TCEP) | 67 63 (48 hr) | 1 | Buffer | 11.8 | 5 | 11.8 | 30 | Mar. 19, 2013 | Old |
| 15 (0.6 mM TCEP) | 60 | 1 | Buffer | 11.8 | 5 | 11.8 | 30 | Mar. 19, 2013 | Old |
| 16) | 54 | 1 | Buffer | 11.8 | 5 | 11.8 | 30 | Mar. 24, 2013 | Old |
| 17 (0.4 mM TCEP) | 72 | 1 | Buffer | 11.8 | 5 | | 30 | Mar. 24, 2014 | Old |
| 18 | 67 | 1 | Buffer | 11.8 | 5 | 11.8 | 30 | Apr. 3, 2014 | New |
| 19 (0.4 mM TCEP) | 75 | 1 | Buffer | 11.8 | 5 | 11.8 | 30 | Apr. 3, 2014 | New |
| 20 (0.4 mM TCEP, added before Cys) | 61 | 1 | Buffer | 11.8 | 5 | 11.8 | 30 | Apr. 24, 2014 | Old |
| 21 (0.4 mM TCEP) | 73 | 1 | Buffer | 11.8 | 5 | 11.8 | 30 | 4/48/2013 | New |
| 22 (0.4 mM TCEP) | 74 | 1 | Buffer | 11.8 | 5 | 11.8 | 30 | Apr. 28, 2013 | New |
| 23 (0.4 mM TCEP, added at 5 min) | 67 | 1 | Buffer | 11.8 | 5 | 11.8 | 30 | May 14, 2013 | New |
| 24 | 59 64 (28 hr) | 1 | Buffer | 11.8 | 5 | 11.8 | 30 | May 20, 2013 | New |

TABLE 1-continued

Summary of all folding reactions

| | | Method Variables | | | | | | |
|---|---|---|---|---|---|---|---|---|
| Run | Yield (%) | hPSS concentration (g/L) | Cysteine addition | pH of cys addition | Dilution temp (° C.) | Dissolution pH | time of dissolution (min) | Date | Batch Date* |
| 25 (0.4 mM TCEP) | 69 | 1 | Buffer | 11.8 | 5 | | 45 | May 27, 2014 |
| 26 (0.8 mM TCEP, added at 5 and 10 min) | 66 | 1 | Buffer | 11.8 | 5 | 11.8 | 45 | May 27 2014 |

TABLE 2

Optimization of hPSS dissolution and folding conditions

| Condition | Improvement in Yield |
|---|---|
| Newer lot preparation date (MR-KPB-hPSS, KPB TFF1, QS5163, Lot# A706083, Prepared 13 Jan. 2010) | 5% compared to older lot preparation date (MR-KPB-hPSS, KPB TFF1 Retentate, Lot# A489010, Prepared 24 Apr. 2008) |
| Dilution using 5° C. water, pH 11.8 | 16% (compared to dilution using 20° C. water) |
| pH 11.8 hPSS dissolution | 22% or 32% (compared to dissolution at pH 8.5 or 13) |
| 30 minute dissolution time; 200 rpm for 400 mL folding solution | Sufficient time to dissolve hPSS to monomers at 4° C. and pH 11.8; No change in size after 30 min |
| pH 11.8 cysteine addition | >20% (compared to addition at pH 13) |
| Cysteine addition as buffer | 16% (compared to addition as solid) |
| [TCEP]:[surface thiols] = 1:1 | Up to 18% |
| TCEP or DTT addition 10 minutes after cysteine addition | 7-14% (compared to no TCEP or DTT addition) |

Frozen Materials

The freezing and thawing of hPSS were found to affect folding yield. S. Chen found that thawing the hPSS stock solution overnight in a cold room (4° C.) improved yield compared to when hPSS was thawed at room temperature or in a room-temperature water bath (Chen, 2010b). As seen in Table 1, hPSS lots that were frozen for longer periods of time and encountered more thawing and re-freezing tended to have lower folding yields. Reducing thermal shock prior to dissolution can therefore improve folding yield.

Dissolution

FCS measurements show that electrostatic and hydrophobic interactions have potential to induce aggregation. The aggregation of hPSS can be mitigated by dilution and/or dissolution at high pH and low temperature (4° C.). The non-covalent interactions evaluated during folding were salt concentration, dilution temperature, dissolution time, dissolution pH, pH of cysteine addition, and cysteine addition as solid/buffer.

Figure 8:
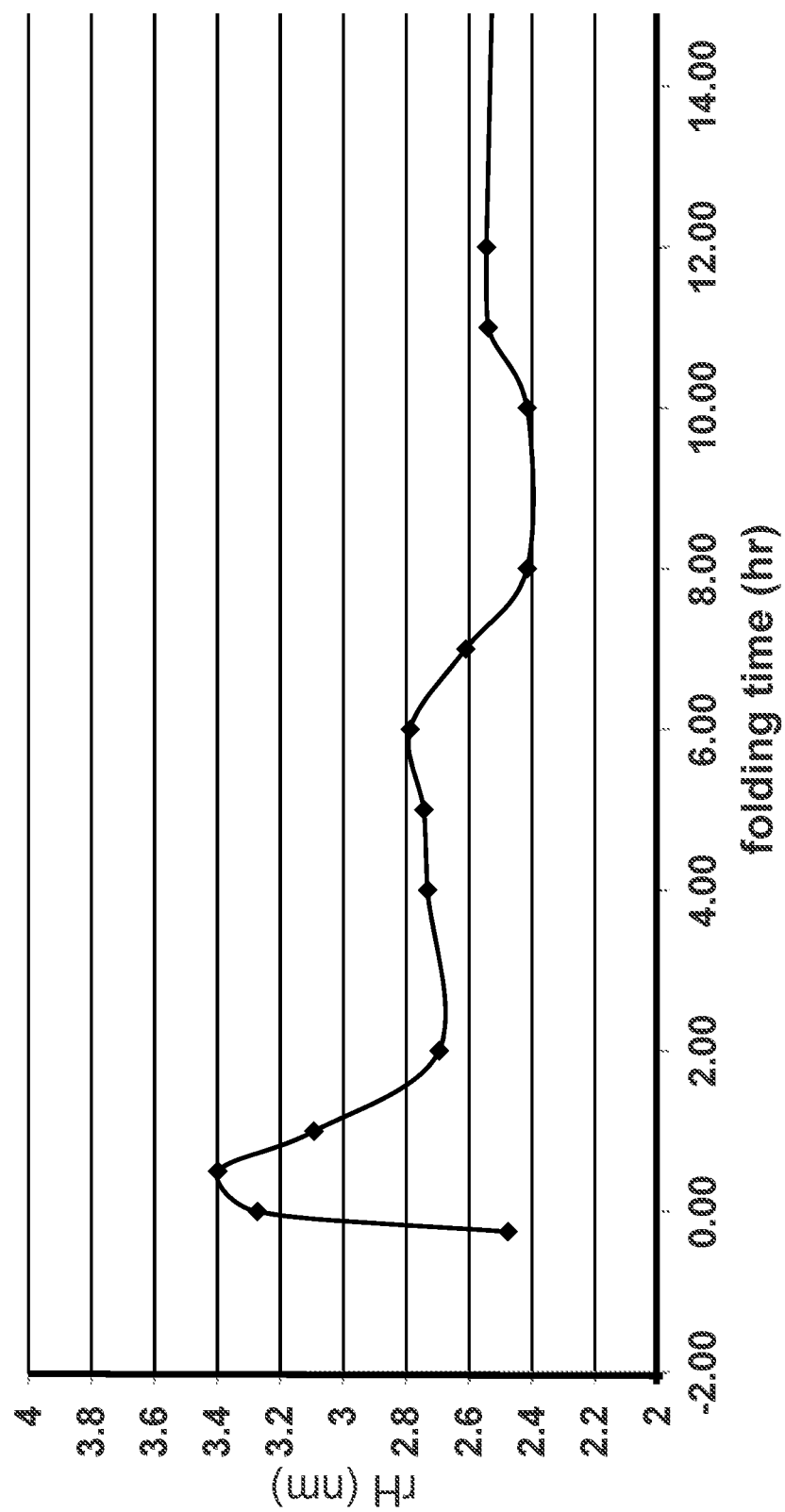
FIG. 8 is a graph of the hydrodynamic radius from FCS for folding of 1 g/L hPSS with dissolution and cysteine addition at pH 13. The first data point shown was for hPSS at −0.25 hr (15 min before cysteine addition). Solid cysteine-HCl was added to obtain 2.1 mM final concentration at 0 hr.
Figure 9:
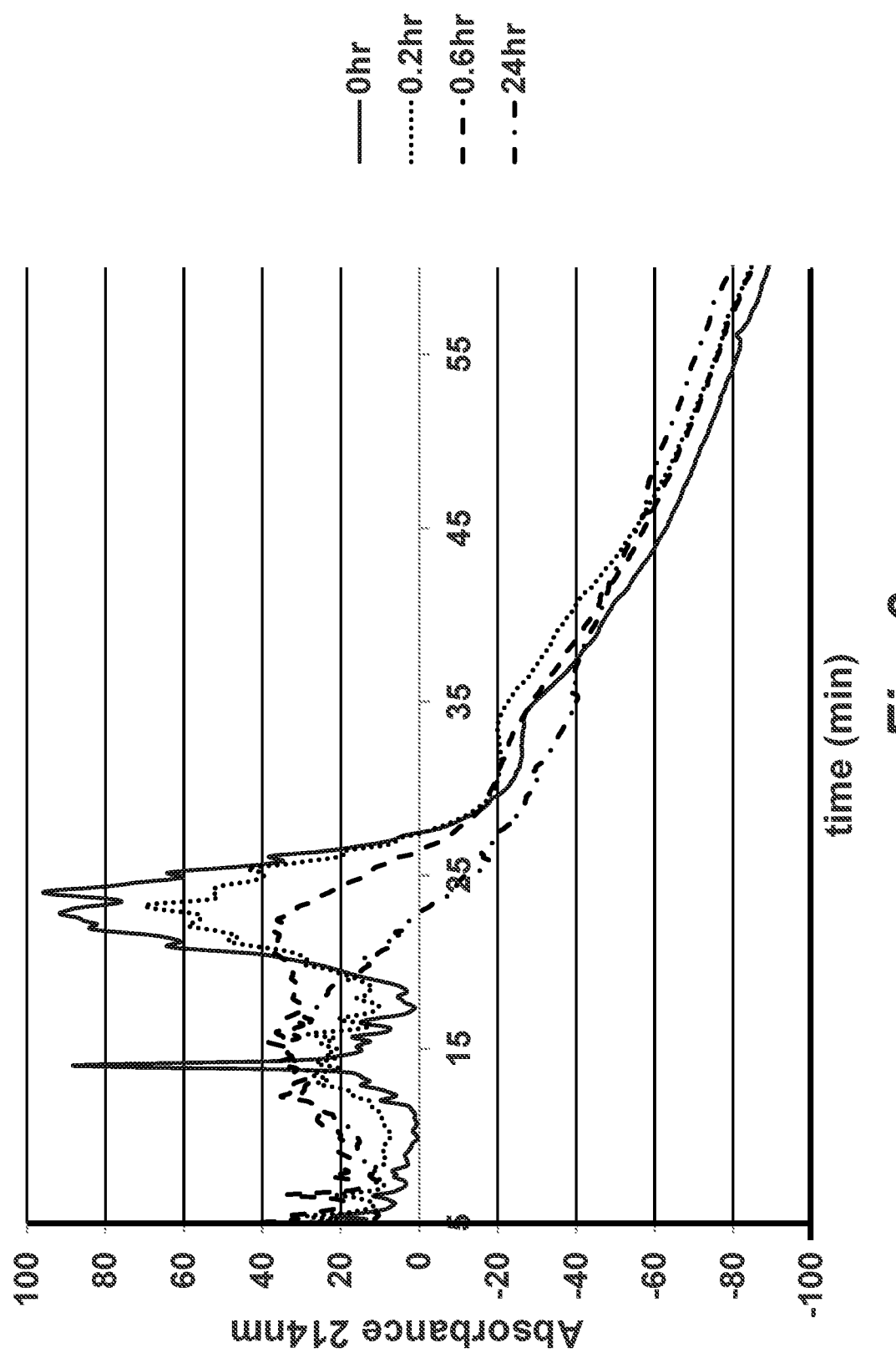
FIG. 9 is a graph of the RP-HPLC chromatograms for folding of 1 g/L hPSS with dissolution and cysteine addition at pH 13. Solid cysteine-HCl was added to obtain 2.1 mM final concentration at 0 hr.

The dissolution conditions for hPSS were found to have a significant effect on yield. When hPSS is dissolved at pH 13, as in Run 1, the folding yield is negligible. The FCS data in FIG. 8 show that the hydrodynamic radius is less than 4 nm throughout the folding and stabilizes as 2.5 nm after 3 hrs. From the Run 1 RPC chromatogram in FIG. 9, it can be concluded that the yield loss is due to misfolding and aggregation. The 0 hr chromatogram shows that a large amount of misfolded intermediates (90%) and a small amount of correctly folded hPI (10%) are present at the beginning of folding. Over the course of folding, the misfolding peak decreases from 90% to 46%, indicating the formation aggregates from misfolded monomers. The native hPI peak at the end of folding cannot be distinguished from the misfolded monomers. The low yield for Run 1 can be attributed to the high dissolution pH and the addition of cysteine at a pH significantly higher than the thiol $pK_A$.

When hPSS is dissolved at pH 13 and cysteine is added at pH 11.8, as in Run 5, the yield increases to 25%. This yield is lower than previous folding data in which hPSS is dissolved at pH 11.8 (Chen, 2010a).

The dissolution of hPSS at pH 13 likely resulted in the formation of non-native 1S bonds; a large fraction of the intermediates with non-native bonds did not reshuffle to the native form after 24 hrs folding, resulting in misfolded intermediates and aggregates.

Figure 10:
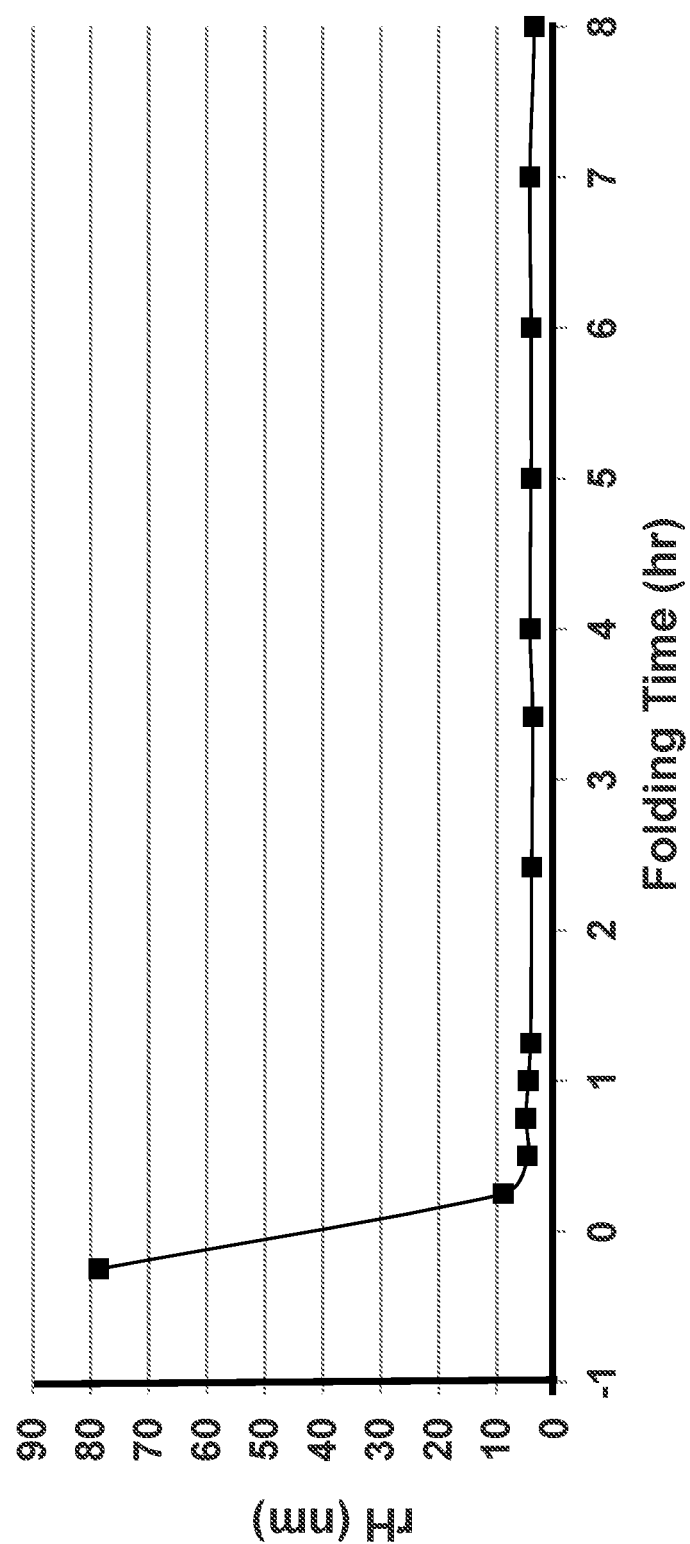
FIG. 10 is a graph of the average hydrodynamic radius from FCS for folding of 1 g/L hPSS with dissolution at pH 8.5. The first data point shown was for hPSS at −0.25 hr (15 min before cysteine addition). Solid cysteine-HCl was added at 0 hr to obtain 2.1 mM.

When hPSS was dissolved without pH adjustment (pH 8.5) as in Run 2, the hydrodynamic radius remained high at the end of dilution as seen FIG. 10. The addition of cysteine at pH 8.5 resulted in precipitates for which the FCS auto correlation function could not be fitted. During folding, the pH was raised to pH 10.8, resulting in re-dissolution of the large aggregates; after 15 minutes of folding, the $r_H$ decreased to 8.9 nm.

Figure 11:
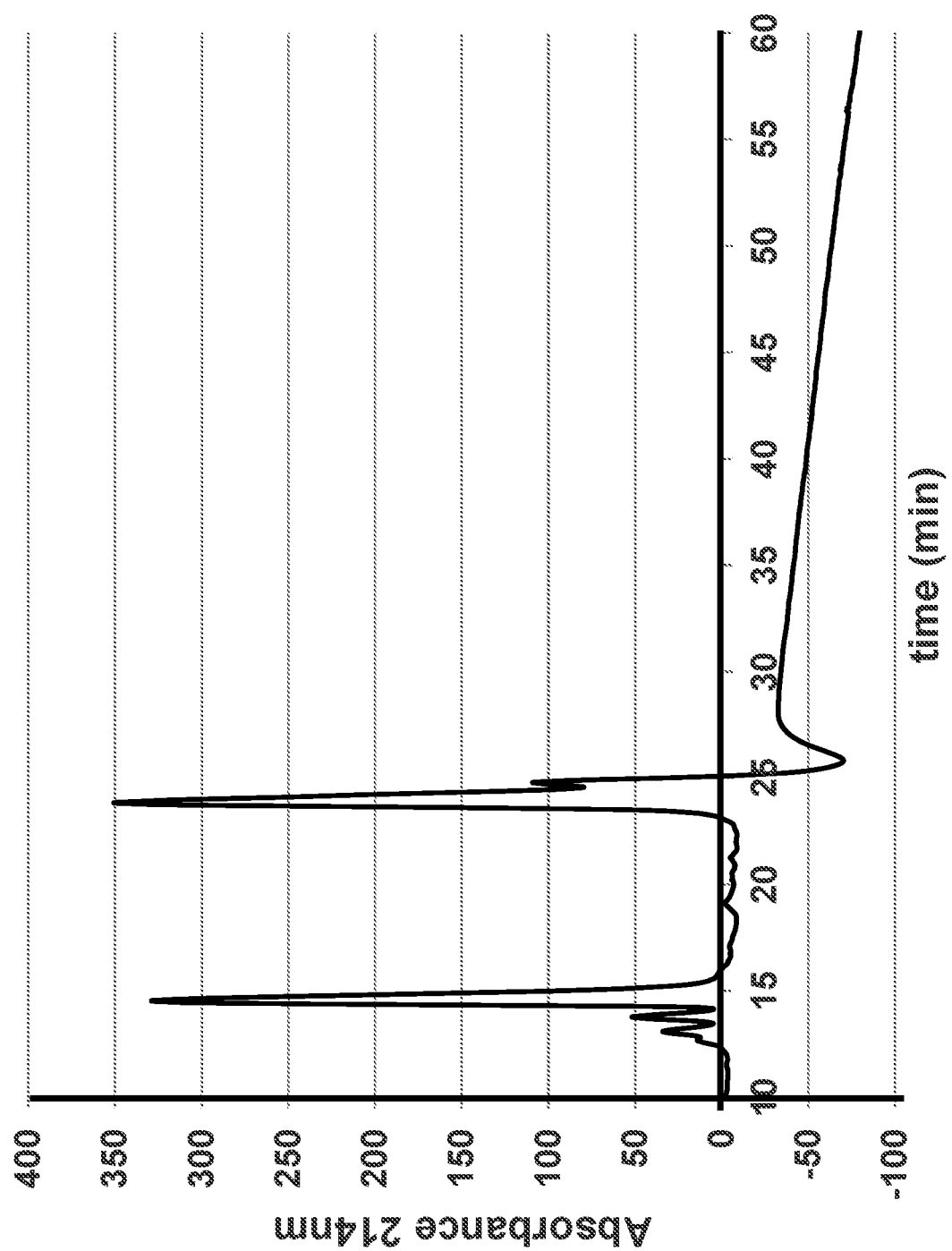
FIG. 11 is graph of the RP-HPLC chromatogram at 24 hours for folding at pH 10.8 The dissolution was at pH 8.5. Initial hPSS concentration was 1 g/L and [Cys]:[thiol] ratio=3.5.

After 1 hr, the $r_H$ stabilized at approximately 4 nm. Though the radius decreased, the folding resulted in a 35% yield, which is lower than expected for 1 g/L hPSS. This yield loss is due primarily to misfolding, as seen in FIG. 11. The area under the monomer misfolding peak (retention time of 24 min) indicates a yield loss of 46%, and 19% of the yield is lost to aggregation (SEC results, not shown).

Figure 12:
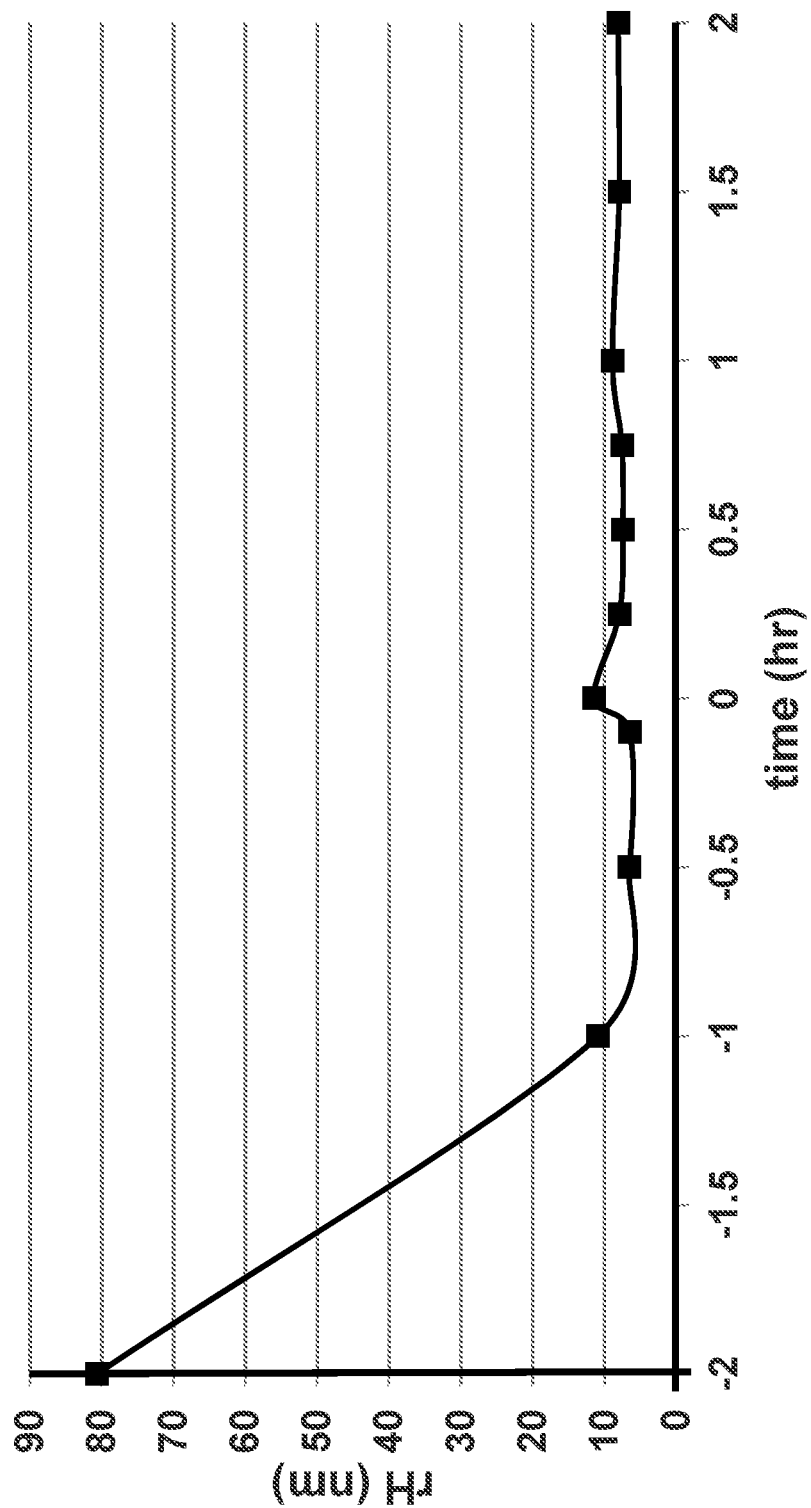
FIG. 12 is a graph of the average hydrodynamic radius from FCS for folding of 1 g/L hPSS in 10 mM PBS. The beginning of hPSS dissolution is shown at −2 hr. Cysteine was added to 2.1 mM final concentration at 0 hr.
Figure 13:
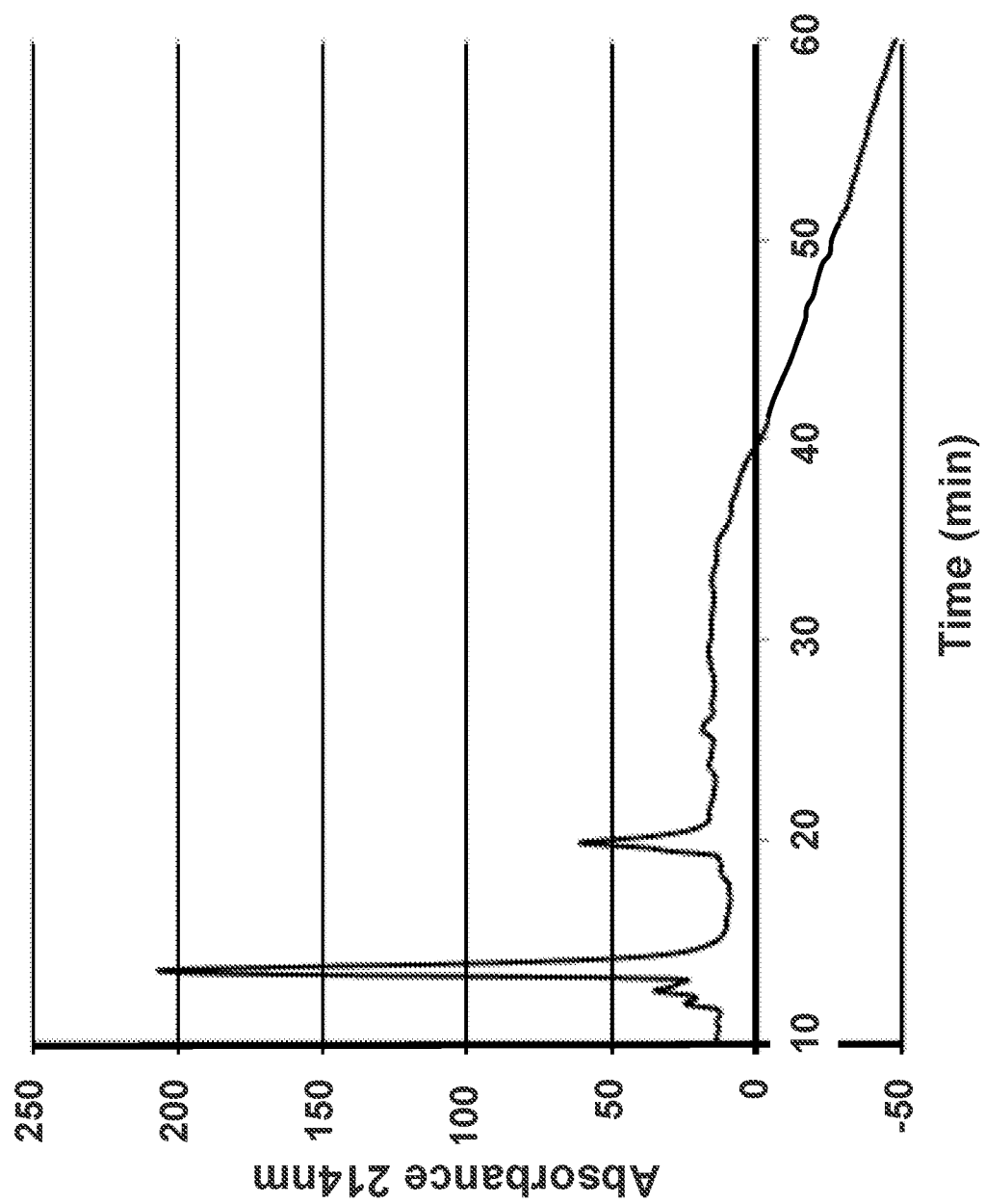
FIG. 13 is graph of the RP-HPLC chromatogram at 24 hr of folding of 1 g/L hPSS in 10 mM PBS at pH 10.8. Cysteine was added as a buffer to 2.1 mM final concentration at 0 hr.

The dissolution of hPSS at room temperature was found to decrease folding yield (Run 7 and 9). In both runs, the hPSS radius at the end of dilution was high-4 nm and 7.5 nm respectively—and the $r_H$ stabilized at 3 nm after 3 hr of folding. In all runs, the addition of cysteine was found to cause rapid flocculation of hPSS. In an effort to mitigate this increase in $r_H$ after cysteine addition, hPSS was folded in 10 mM PBS. The FCS data in FIG. 12 show that the $r_H$ remained high during folding, and stabilized at 8 nm after 1 hr of folding. The RPC chromatogram after 24 hr of folding (FIG. 13) indicates a yield of 35% native hPI, with 16% of the yield being lost to misfolding. The majority of the yield in Run 10—49%—was lost to aggregation.

Folding Conditions

Figure 14:
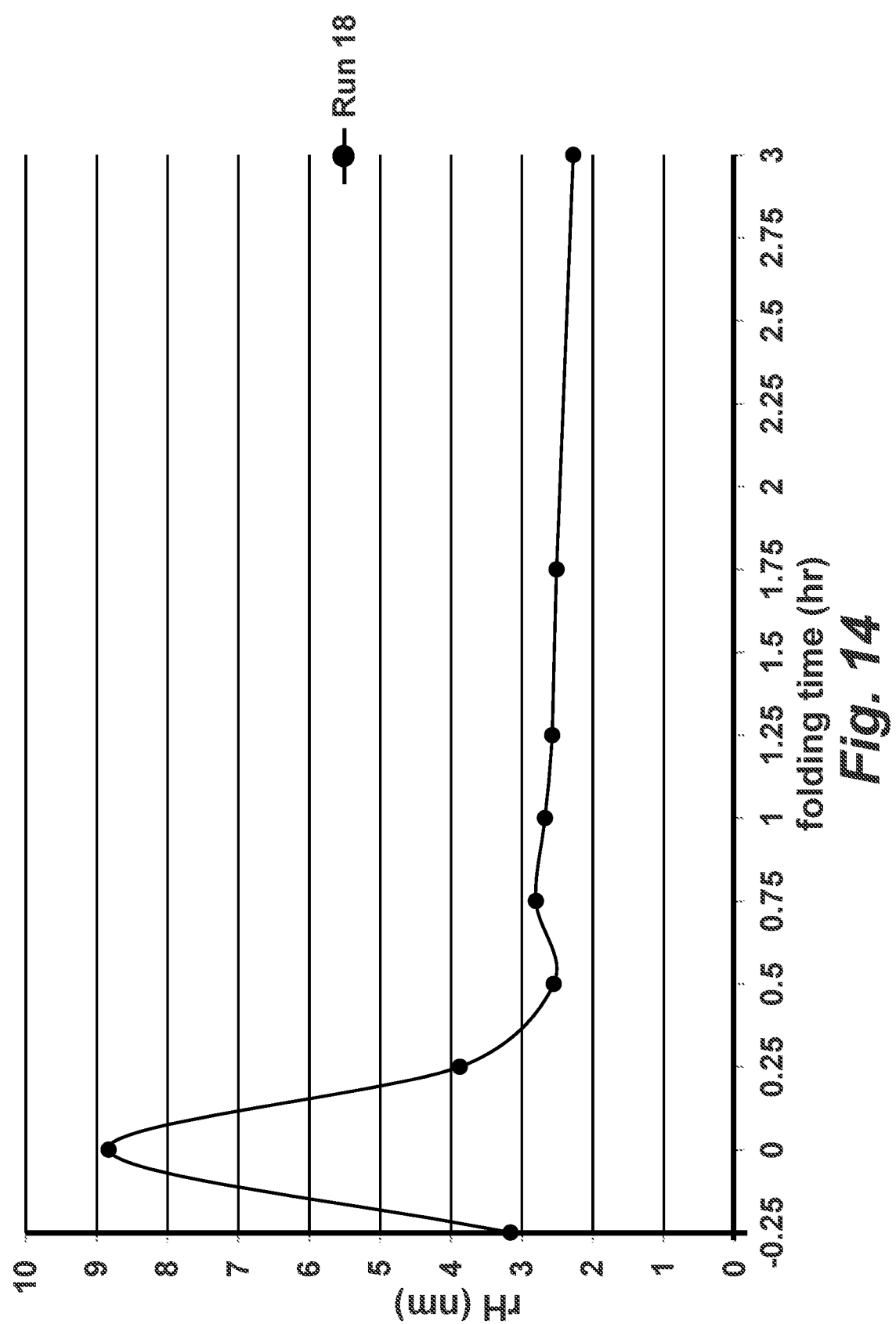
FIG. 14 is a graph of the average hydrodynamic radius from FCS for folding of 1 g/L hPSS. The beginning of hPSS dissolution is shown at −15 min. Cysteine buffer was added at 0 hr to 2.1 mM final concentration.

The best folding yields were achieved when hPSS was dissolved at pH 11.8 and when cysteine was added as a pH 1.5 buffer. The addition of cysteine as a solid (cysteine-HCl) resulted in low protein solubility at the beginning of folding and ultimately in low yields. The addition of cysteine as a pH 1.5 buffer resulted in higher yields (54-67%), likely due to improved mixing conditions and reduced local pH fluctuations. At these conditions, hPSS was still found to flocculate upon cysteine addition, as shown in FIG. 14, likely due to the rapid reduction in pH. Upon correcting the pH to folding conditions (pH 10.8), the hydrodynamic radius of hPSS gradually returned to an apparently monomeric form in the first half hour of folding.

Poor dissolution of hPSS before folding was found to result in yield loss due to aggregation and misfolding. A high $r_H$ during folding appears to coincide with significant folding yield loss due to aggregation. A high hPSS $r_H$ at the end of dissolution (>4 nm) always resulted in yields less than 45%. A low hPSS $r_H$ at the end of dissolution (<4 nm) did not always correlate to a high yield, however; misfolded monomers are similar in size to hPSS and native hPI, thus these isoforms cannot be distinguished by FCS. RP-HPLC is needed to quantify the various forms of monomeric intermediates. SEC is needed to quantify monomers, misfolded monomers, dimers, trimers, and larger aggregates.

Additives

The covalent interactions evaluated were type of reducing agent (cysteine, TCEP, or DTT), time of reducing agent addition, and TCEP concentration. TCEP and DTT are strong reducing agents that break surface disulfide bonds. TCEP is consumed irreversibly to break disulfide bonds. TCEP has been found to act only on the exterior disulfide bonds of proinsulin or insulin while leaving the interior bond intact. DTT acts reversibly to reduce disulfide bonds, however forms a stable cyclic structure upon oxidation. Due to the ability of TCEP and DTT to reduce surface disulfide bonds, these reducing agents have potential to reduce aggregation via intermolecular disulfide bonds.

The time of TCEP addition was found to affect folding yield. Adding TCEP 10 minutes after the addition of cysteine resulted in the highest yields, up to 75%. Adding TCEP at 5 min, −5 min (5 min before cysteine), −5 and 15 min, and 5 and 10 resulted in yields of 67%, 60%, 59%, and 66% respectively. A size exclusion chromatography assay was used to determine the source of yield loss. A summary of the folding results at 24 hr is shown in Table 3. Without the addition of a strong reducing agent, significant yield is lost to dimerization, while equal amounts of the yield are lost to trimers and large aggregates. When TCEP is added at 5 min or −5 and +15 min, there are fewer dimers but more misfolded monomers. The yield recovered by adding TCEP at 10 min appears to be from breaking down large aggregates, trimmers, and dimers, while the yield recovered by adding DTT is from breaking down the large aggregates and trimers.

Figure 15A:
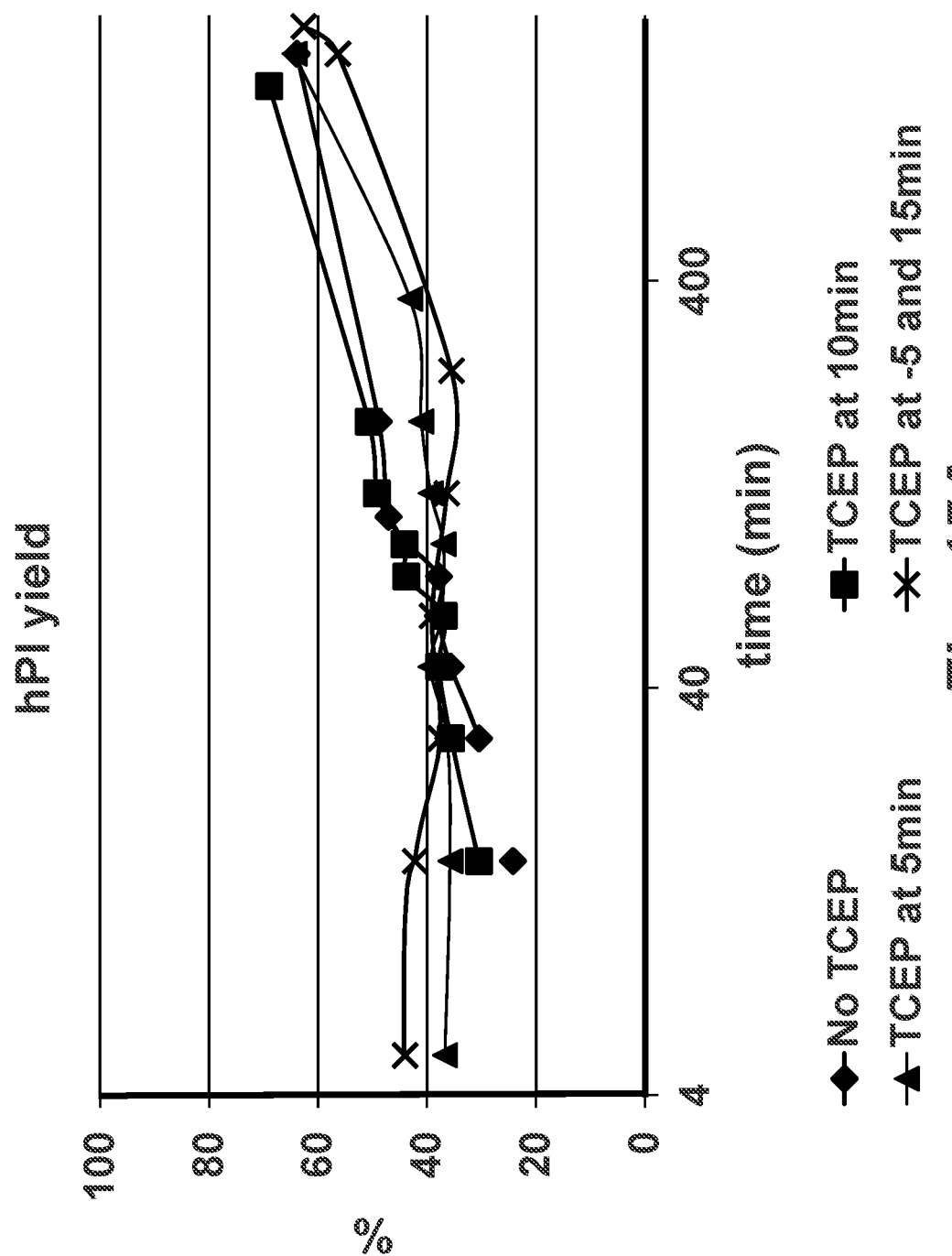
FIGS. 15A-15C are graphs of the monomer yields (mol %) during folding of hPSS using one folding agent (cysteine) or two folding agents (cysteine and TCEP), depicting the hPI yield (FIG. 15A), unfolded/extended monomer (FIG. 15B) and misfolded monomer (FIG. 15C) as a function of time.
Figure 15B:
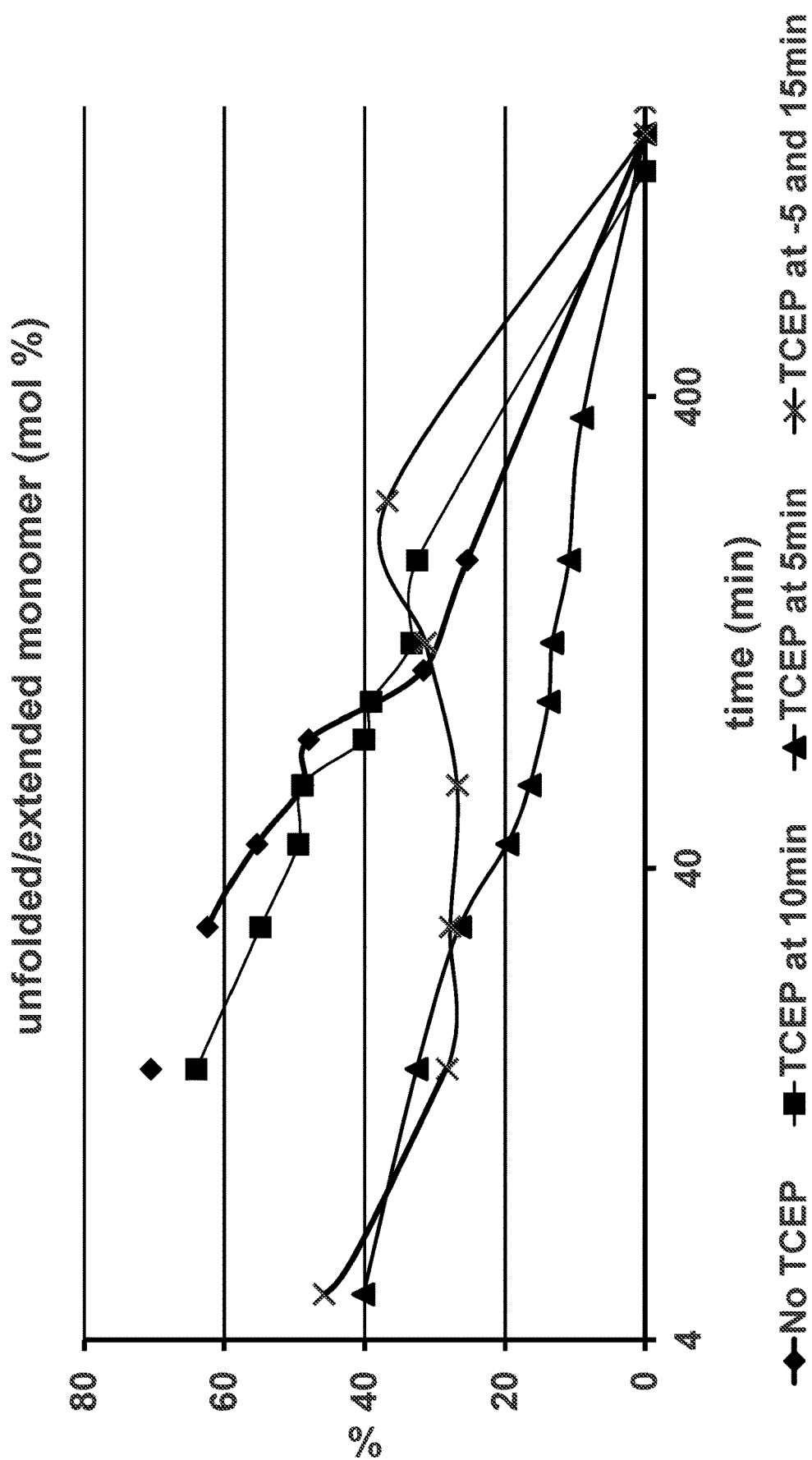
Figure 15C:
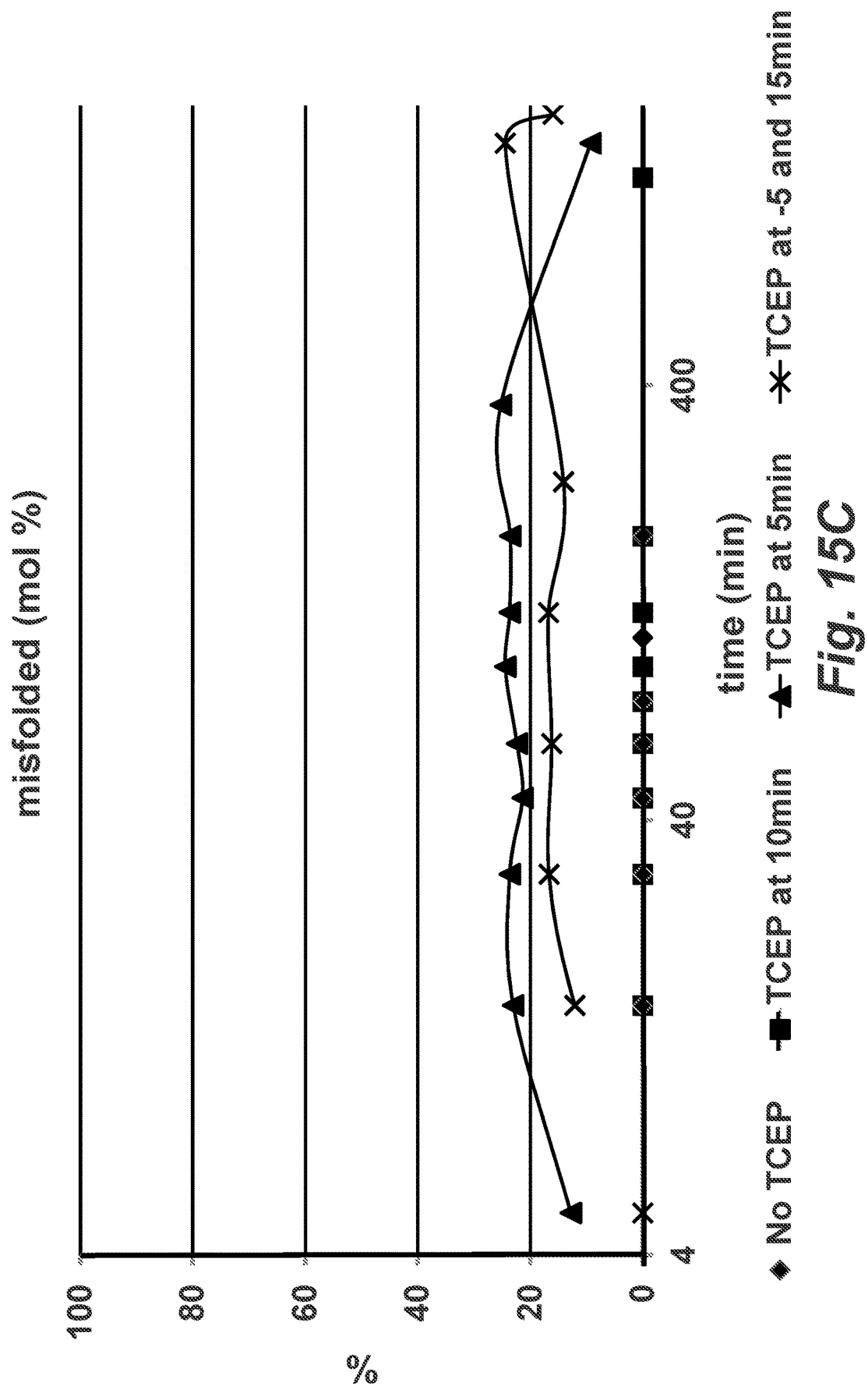

Shown in FIG. 15A, hPI is generated over 24 hrs from the conversion of an extended/unfolded monomer. When TCEP is added at or before 5 min, a misfolded monomer is generated in the first 20 min of folding that persists over 24 hrs.

The time evolution of aggregates is seen in FIGS. 16A-16C. Without TCEP, dimers are generated in the first 2 hrs of folding and are not broken down. Trimers are formed in the first 200 min. When TCEP is added at 10 min, dimers and trimers form, but are partially broken down. In all runs, a large aggregate was formed that eluted before the dimers and trimers in the SEC assay. These large aggregates began to form within the first 5-10 min of folding. When TCEP was added at 5 min, some of the large aggregates were broken down into trimers, however these trimers were not further reduced to dimers or monomers. In the first 5-10 minutes of folding, there appears to be a competition between forming the first native disulfide bond (A6-A11) and forming aggregates. The large aggregates form more quickly than the dimers and trimers and are likely the result of local pH changes when cysteine is added to the folding broth. The extended monomers without any native disulfide bonds are also prone to the formation of intermolecular disulfide bonds, resulting in aggregation. After the large aggregates have formed, unfolded monomers are gradually converted to hPI, dimers, and trimers. TCEP and DTT improve folding yield by reducing the rates of forming dimers, trimers, and large aggregates.

TABLE 3

Summary of 24 hr folding yields and yield loss with TCEP or DTT added during folding

| | Run | | | | |
|---|---|---|---|---|---|
| | No TCEP (Run 18) | TCEP at 10 min (Run 19) | DTT at 10 min (Run 21) | TCEP at 5 min (Run 23) | TCEP at −5 and +15 min (Run 24) |
| RP-HPLC Yield % | 67 | 75 | 73 | 67 | 59 |
| SEC-HPLC Estimated Yield % | 64 | 73 | 77 | 64 | 63 |
| % all monomers* | 64 | 73 | 77 | 71 | 75 |
| % unfolded monomer* | 0 | 0 | 0 | 0 | 0 |
| % misfolded monomer* | 0 | 0 | 0 | 7 | 12 |
| % dimer* | 14 | 10 | 10 | 10 | 7 |
| % trimer* | 11 | 10 | 6 | 15 | 9 |
| % large aggregate* | 11 | 7 | 6 | 4 | 9 |

*determined from SEC assay integration

To determine the optimum [TCEP]:[thiol] ratio, foldings were conducted with 1 g/L hPSS in which TCEP was added to the folding broth 10 minutes after the addition of cysteine. The optimal TCEP concentration is 0.4 mM; this is equivalent to a 1:1 [TCEP]:[surface thiol] ratio. Below the optimal [TCEP]:[thiol] ratio, insufficient TCEP is present to prevent dimer and trimer formation. Above the optimal [TCEP]:[thiol] ratio, it appears that TCEP reduces already formed native disulfide bonds. Both the time of addiction and concentration of TCEP are therefore important in improving yield. The use of TCEP or DTT in tandem with cysteine improve folding yield because they reduce surface disulfide bonds. When added at 10 min, TCEP and DTT break the surface disulfide bonds irreversibly to reduce dimers, trimers, and large aggregates to monomers. Cysteine is a reversible reducing agent and thus reshuffles the non-native bonds of monomers to the native form (hPI).

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A method of refolding a solubilized cysteine-containing protein to its native form, the method comprising
adding a reversible reducing agent to a solution containing the solubilized cysteine-containing protein to initiate folding of the cysteine-containing protein, wherein the reversible reducing agent is added at a ratio of [reversible reducing agent]:[thiols in the cysteine-containing protein] of 3:1 to 4:1; and
adding an irreversible reducing agent to the solution at a time after the initiation of folding to breakdown aggregates of the cysteine-containing protein.

2. The method of claim 1, wherein the time after the initiation of folding is when the concentration of the dimer in the solution is 5 mol % to 12 mol % based upon the concentration of the cysteine-containing protein.

3. The method of claim 1, wherein the time after the initiation of folding is when the concentration of the dimer in the solution is 1.5 to 3.0 times the concentration of the dimer in the solution prior to the addition of the reversible reducing agent.

4. The method of claim 1, wherein the time after the initiation of folding is 5 minutes to 15 minutes.

5. The method of claim 1, wherein the irreversible reducing agent has a redox potential of −0.3 V to −0.35 V at a pH above 7.0, and wherein the irreversible reducing agent has a redox equilibrium constant of $10^3$ to $10^5$.

6. The method of claim 1, wherein the irreversible reducing agent is added at a ratio of [irreversible reducing agent]:[thiols in the cysteine-containing protein] of 0.5:1 to 0.8:1.

7. The method of claim 1, wherein the cysteine-containing protein is a recombinant protein selected from the group consisting of an enzyme, an antibody, an antigen, a hormones, and a cytokine.

8. The method of claim 7, wherein the recombinant protein is an inclusion body isolated from an *Escherichia coli* expression system.

9. The method of of claim 1, wherein the cysteine-containing proteins is insulin, an insulin analogue, or a proinsulin.

10. The method of claim 1, wherein the concentration of the cysteine-containing protein in the solution prior to addition of the reversible reducing agent is 0.3 g/L to 1 g/L.

11. The method of claim 1, further comprising dissolution of the cysteine-containing protein at an alkaline pH to form the solubilized cysteine-containing protein.

12. The method of claim 11, where the alkalinepH is 11.5-12.5.

13. The method of claim 11, where the temperature is 4° C. to 8° C.

14. The method of claim 1, wherein the pH of the solution after the addition of the reversible reducing agent is 10.75 to 10.85.

15. The method of claim 1, wherein the reversible reducing agent is cysteine-HCl dissolved to a 200 mM to 900 mM at 4° C. to 8° C. and acidic pH.

* * * * *